United States Patent [19]

Rogers et al.

[11] Patent Number: 4,675,526
[45] Date of Patent: Jun. 23, 1987

[54] METHOD AND APPARATUS FOR 3-D ENCODING

[76] Inventors: Joel G. Rogers, 3804 West 26th Avenue, Vancouver, B. C., Canada, V6T 2A3; Dwight P. Saylor, 39 Otsego Rd., Worcester, Mass. 01609

[21] Appl. No.: 723,341

[22] Filed: Apr. 15, 1985

[51] Int. Cl.⁴ ............................................. G01T 1/208
[52] U.S. Cl. .................................. 250/363.5; 250/368
[58] Field of Search .......................... 250/363 S R, 368

[56] References Cited

U.S. PATENT DOCUMENTS 3,676,676  7/1972  Somer .
3,717,762  2/1973  Grenier et al. .................... 250/363.5
3,944,835  3/1976  Vosburgh .
4,454,424  6/1984  Strauss et al. ........................ 250/368

FOREIGN PATENT DOCUMENTS 1529215 10/1978 United Kingdom ................. 250/368

OTHER PUBLICATIONS

"A Thick Anger Camera For Gamma-Ray Astronomy", W. R. Cook et al., Nuclear Science, vol. NS-32, No. 1, Feb. 1985.
"Newly Developed Photomultiplier Tubes with Position Sensitivity Capability," Citation and date unknown.

Primary Examiner—Janice A. Howell
Assistant Examiner—David P. Porta
Attorney, Agent, or Firm—Finnegan, Henderson, Farabow, Garrett & Dunner

[57] ABSTRACT

A novel 3-D encoding scintillation camera which has improved light collection and internal light spreading properties which enhance its use in the field of nuclear medicine is disclosed. The scintillation camera, which is useful for human organ imaging, comprises: (a) a scintillator means of thickness coordinated to correspond generally with the energy of gamma-rays received; (b) photodetector means for detecting the scintillation photons; (c) background light filter means positioned between the scintillator means and the plurality of photodetectors; (d) analog-to-digital converter network means capable of processing pulses from the plurality of photodetectors; and (e) means for analyzing each scintillation event before storing the information in a digital memory. Reflecting means capable of transmitting gamma-rays and reflecting the resulting light photons at about a 180° angle may be optically coupled to the entrance face of the scintillator means.

22 Claims, 17 Drawing Figures

▨ = PHOTODETECTOR SAMPLING ELEMENT
▷ = LINEAR PULSE SUMMING AMPLIFIER

| EVENT | P0 | P1 | P2 | P3 | P4 | P5 | P6 | P7 | P8 | P9 | P10 | P11 | PARAM 1 | PARAM 2 | PARAM 3 |
|---|---|---|---|---|---|---|---|---|---|---|---|---|---|---|---|
| 1 | 0 | 0 | 0 | 0 | 0 | 0 | 0 | 13 | 0 | 0 | 30 | 0 | 43.0 | 0.0 | 0.0 |
| 2 | 0 | 4 | 21 | 81 | 7 | 12 | 0 | 5 | 0 | 0 | 0 | 0 | 130.0 | 3.7 | 7.0 |
| 3 | 0 | 0 | 11 | 0 | 13 | 0 | 0 | 0 | 0 | 0 | 0 | 0 | 24.0 | 3.6 | 3.0 |
| 4 | 0 | 0 | 0 | 0 | 0 | 0 | 0 | 0 | 0 | 66 | 0 | 15 | 81.0 | 9.9 | 3.0 |
| 5 | 0 | 0 | 10 | 0 | 45 | 0 | 0 | 0 | 0 | 0 | 0 | 0 | 55.0 | 4.1 | 3.0 |
| 6 | 0 | 0 | 42 | 6 | 18 | 9 | 2 | 0 | 0 | 0 | 0 | 0 | 77.0 | 3.5 | 5.0 |
| 7 | 0 | 0 | 12 | 0 | 54 | 12 | 13 | 0 | 2 | 0 | 0 | 0 | 93.0 | 0.0 | 0.0 |
| 8 | 0 | 0 | 0 | 0 | 0 | 0 | 5 | 5 | 9 | 0 | 0 | 8 | 27.0 | 0.0 | 0.0 |
| 9 | 27 | 34 | 23 | 24 | 18 | 0 | 0 | 0 | 0 | 0 | 0 | 0 | 126.0 | 2.3 | 5.0 |
| 10 | 0 | 0 | 39 | 69 | 46 | 23 | 50 | 4 | 0 | 0 | 0 | 0 | 231.0 | 4.4 | 6.0 |
| 11 | 0 | 13 | 0 | 0 | 23 | 95 | 0 | 0 | 0 | 0 | 0 | 0 | 131.0 | 0.0 | 0.0 |
| 12 | 0 | 0 | 0 | 0 | 0 | 0 | 0 | 0 | 0 | 0 | 12 | 182 | 194.0 | 11.4 | 2.0 |
| 13 | 0 | 14 | 0 | 11 | 77 | 0 | 0 | 0 | 0 | 0 | 0 | 0 | 102.0 | 4.0 | 4.0 |
| 14 | 0 | 0 | 0 | 1 | 77 | 44 | 24 | 24 | 0 | 0 | 0 | 0 | 170.0 | 5.5 | 5.0 |
| 15 | 0 | 20 | 4 | 0 | 52 | 67 | 3 | 6 | 0 | 0 | 0 | 0 | 152.0 | 4.7 | 7.0 |
| 16 | 0 | 0 | 0 | 0 | 0 | 3 | 0 | 37 | 21 | 12 | 9 | 0 | 82.0 | 8.3 | 6.0 |
| 17 | 0 | 0 | 0 | 0 | 0 | 0 | 0 | 0 | 78 | 29 | 0 | 0 | 107.0 | 8.8 | 2.0 |
| 18 | 0 | 0 | 42 | 59 | 127 | 47 | 7 | 0 | 0 | 0 | 0 | 0 | 282.0 | 4.2 | 5.0 |
| 19 | 0 | 0 | 96 | 0 | 29 | 12 | 0 | 0 | 0 | 0 | 0 | 0 | 137.0 | 3.2 | 4.0 |
| 20 | 0 | 0 | 0 | 0 | 9 | 80 | 0 | 0 | 0 | 0 | 0 | 0 | 89.0 | 5.4 | 2.0 |
| 21 | 0 | 0 | 32 | 0 | 0 | 7 | 0 | 0 | 0 | 0 | 0 | 0 | 39.0 | 0.0 | 0.0 |
| 22 | 0 | 0 | 20 | 52 | 5 | 51 | 16 | 0 | 0 | 0 | 0 | 0 | 144.0 | 4.4 | 5.0 |
| 23 | 0 | 0 | 18 | 25 | 72 | 42 | 31 | 10 | 0 | 0 | 0 | 0 | 198.0 | 4.9 | 6.0 |
| 24 | 0 | 55 | 34 | 42 | 11 | 6 | 0 | 0 | 0 | 0 | 0 | 0 | 148.0 | 2.7 | 5.0 |
| 25 | 0 | 0 | 5 | 0 | 15 | 36 | 14 | 0 | 0 | 0 | 0 | 0 | 70.0 | 5.3 | 5.0 |
| 26 | 0 | 0 | 0 | 0 | 5 | 6 | 0 | 5 | 57 | 125 | 186 | 145 | 529.0 | 10.2 | 8.0 |
| 27 | 1 | 54 | 9 | 0 | 0 | 0 | 0 | 0 | 0 | 0 | 0 | 0 | 64.0 | 1.6 | 3.0 |
| 28 | 0 | 0 | 0 | 2 | 4 | 0 | 10 | 0 | 0 | 0 | 0 | 0 | 16.0 | 5.6 | 4.0 |
| 29 | 0 | 0 | 0 | 2 | 0 | 68 | 0 | 5 | 0 | 0 | 0 | 0 | 75.0 | 0.0 | 0.0 |
| 30 | 0 | 5 | 0 | 19 | 0 | 0 | 8 | 0 | 0 | 0 | 0 | 0 | 32.0 | 0.0 | 0.0 |
| 31 | 0 | 6 | 88 | 53 | 82 | 28 | 31 | 0 | 0 | 0 | 0 | 0 | 288.0 | 4.0 | 6.0 |
| 32 | 0 | 0 | 25 | 25 | 98 | 2 | 35 | 0 | 0 | 0 | 0 | 0 | 185.0 | 4.5 | 5.0 |
| 33 | 0 | 0 | 0 | 40 | 19 | 18 | 29 | 0 | 0 | 0 | 0 | 27 | 133.0 | 0.0 | 0.0 |
| 34 | 0 | 8 | 7 | 0 | 5 | 2 | 14 | 0 | 0 | 0 | 0 | 0 | 36.0 | 4.3 | 6.0 |
| 35 | 0 | 0 | 19 | 20 | 0 | 31 | 0 | 0 | 0 | 0 | 0 | 0 | 70.0 | 4.1 | 4.0 |
| 36 | 0 | 0 | 0 | 0 | 0 | 0 | 0 | 11 | 230 | 0 | 51 | 47 | 339.0 | 9.2 | 5.0 |
| 37 | 0 | 0 | 0 | 0 | 0 | 0 | 0 | 0 | 29 | 7 | 0 | 0 | 36.0 | 8.7 | 2.0 |
| 38 | 0 | 0 | 0 | 0 | 41 | 40 | 24 | 1 | 2 | 0 | 0 | 0 | 108.0 | 5.4 | 5.0 |
| 39 | 0 | 0 | 0 | 61 | 54 | 6 | 0 | 0 | 0 | 0 | 0 | 0 | 121.0 | 4.0 | 3.0 |
| 40 | 0 | 0 | 0 | 0 | 96 | 0 | 0 | 0 | 0 | 0 | 0 | 22 | 118.0 | 0.0 | 0.0 |
| 41 | 1 | 13 | 0 | 25 | 93 | 72 | 8 | 0 | 0 | 0 | 0 | 0 | 212.0 | 4.6 | 7.0 |
| 42 | 0 | 0 | 0 | 34 | 33 | 0 | 0 | 0 | 0 | 0 | 0 | 0 | 67.0 | 4.0 | 2.0 |
| 43 | 0 | 5 | 17 | 44 | 0 | 12 | 0 | 19 | 0 | 0 | 0 | 0 | 97.0 | 0.0 | 0.0 |
| 44 | 0 | 1 | 10 | 50 | 13 | 23 | 11 | 15 | 0 | 0 | 0 | 0 | 123.0 | 4.6 | 7.0 |
| 45 | 0 | 0 | 0 | 23 | 0 | 2 | 44 | 0 | 0 | 0 | 0 | 0 | 69.0 | 5.5 | 4.0 |
| 46 | 0 | 0 | 0 | 0 | 126 | 72 | 0 | 0 | 0 | 0 | 0 | 0 | 198.0 | 4.9 | 2.0 |
| 47 | 0 | 0 | 0 | 13 | 87 | 0 | 24 | 0 | 0 | 0 | 0 | 0 | 124.0 | 4.8 | 4.0 |
| 48 | 0 | 0 | 0 | 0 | 98 | 23 | 0 | 0 | 0 | 0 | 0 | 0 | 121.0 | 4.7 | 2.0 |
| 49 | 0 | 0 | 0 | 0 | 67 | 5 | 0 | 0 | 0 | 0 | 0 | 0 | 72.0 | 4.6 | 2.0 |
| 50 | 0 | 0 | 0 | 39 | 128 | 12 | 0 | 3 | 0 | 0 | 0 | 0 | 182.0 | 4.4 | 5.0 |

FIG. 9

METHOD AND APPARATUS FOR 3-D ENCODING

FIELD OF THE INVENTION

This invention relates to a novel scintillation camera useful in the field of nuclear medicine. More particularly, this invention relates to a novel, 3-D encoding scintillation camera which has improved light collection and internal light spreading properties which enhance its use in human organ imaging.

BACKGROUND OF THE INVENTION

Since the invention of the scintillation camera by H. O. Anger (H. O Anger, "Scintillation Camera", Rev. Sci. Instr. 29, pp. 27–33, January, 1958 or U.S. Pat. No. 3,011,057) hospital nuclear medicine departments have relied on it for a wide range of human organ imaging. In order to optimize spatial resolution, the modern scintillation camera has evolved to the point where it employs very thin plates of thallium activated sodium iodide (hereinafter termed NaI) as the active scintillation crystal. Typically, these camera plates measure less than 1 cm in thickness, which thereby results in a very small detection efficiency for the available energies of gamma-rays. Because of the low efficiency, most of the radioactive tracer injected into a subject is wasted because the emerging gamma-rays do not interact in the thin crystal. On the other hand, the amount of radioactive tracer that can be injected is limited to a level which minimizes damage caused by gamma-rays interacting in the subject's body. A compromise must therefore be struck. Because of this, it is often necessary to acquire scan data over an extended period of time to obtain enough statistical accuracy to make good quality images. This situation limits the number of scans that can be performed by a single machine in a given period of time. The slow scan time wastes the time of the hospital staff and burdens the subject with an extended period of immobility.

Another contributing reason for the low detection efficiency in standard nuclear medicine systems is the use of a lead collimator between the subject and detector to define the flight direction of the gamma-rays reaching the camera plate crystal. Because gamma-rays are emitted isotropically from the tracer concentrations in the subject's body, a much greater efficiency could be obtained if a wide range of gamma-ray angles could be accepted at the detector. A system which accomplishes this is the positron emission tomograph (PET). In this equipment, the flight direction of each detected emission event is determined by detecting in a second detector the conjugate gamma-ray which is emitted along the opposite direction. Because the PET detectors are uncollimated, a huge increase in detection solid angle is obtained over the scintillation camera.

In addition to the potential advantage of vastly increased sensitivity, a PET detector offers a much greater selection of tracer chemicals. Virtually every biologically interesting element has a positron emitting isotope, whereas single gamma-emitting isotopes are relatively rare in the table of isotopes. PET tracers can be manufactured which are exact chemical copies of metabolically active components of the body, whereas single photon tracers must utilize chemicals such a technetium or thallium which can only partially mimic biological function.

The problem of low detection efficiency in a camera plate is of even greater concern in PET because of high gamma-ray energy (511 keV) and because detectors are required to simultaneously detect two gamma-rays. When two conventional scintillation cameras are used in coincidence for PET the small efficiency of the camera plate is squared, which results in such a small detection efficiency that the gains made by increasing the solid angle are largely cancelled.

In order to avoid these problems, tomographs designed especially for PET typically utilize arrays of small crystals each coupled to a small photomultiplier tube (PMT). These machines obtain fair spatial resolution and good efficiency, but have not been adopted widely for routine clinical studies. Poor acceptance is believed to be partially due to the restrictive detector design. The small crystals are long and narrow and thus it is necessary to employ a rigid ring geometry with the imaged subject volume near the centre of the ring. This rigid geometry creates the need for a large number of crystals to cover the solid angle at a large distance from the subject. Such machines are expensive and inflexible compared to conventional scintillation cameras. In addition, the long narrow crystal shape causes a severe degradation of resolution in regions of the subject away from the ring centre. This distorts the image of small objects so that an object which appears spherical at the centre appears oblong at the edge of the field of view.

A complete three-dimensional fitting procedure has been disclosed under the title, "A Thicker Anger Camera for Gamma-Ray Astronomy", California Institute of Technology, at a conference in November 1984, published IEEE Trans. Nucl. Sci. NS-32, 1985. The procedure by W. R. Cook, M. Finger and T. A. Prince, utilizes a thick crystal Anger camera of otherwise standard configuration. The off-line fitting procedure reported has been shown to improve horizontal position resolution substantially, but does not appear adaptable to on-line event-by-event analysis, especially in high resolution devices. In addition, the procedure described by Cook et al. utilizes a standard NaI camera plate crystal which is inferior to the subject invention in its ability to determine the depth of interaction because the scintillation photons are propagated in an uncontrolled way by the diffuse reflector material surrounding the crystal.

The use of corner reflectors in scintillation cameras has been disclosed in U.S. Pat. No. 3,944,835, Vosburgh, Mar. 16, 1976, but this patent does not recognize the use of corner reflectors to create a depth-independent source distribution. In addition, the corner reflector disclosed by Vosburgh uses a metal material to cause reflection, as is the case with a conventional mirror, rather than a polished surface, to cause total internal reflection.

A system for detecting radiant energy and yielding an output which is indicative of the position of the X, Y plane of the input surface of the detection element is disclosed in U.S. Pat. No. 3,676,676, Somer, July 11, 1972. The Somer system does not relate to scintillation cameras.

SUMMARY OF THE INVENTION

This invention is directed to an improved type of scintillation camera which is useful for human organ imaging in the field of nuclear medicine. The camera is designed to have good spatial resolution and superior detection efficiency of gamma-rays in the energy range above 100 keV. The camera is especially suited to the crucial positron emission energy of 511 keV. Improved efficiency allows many common types of nuclear medicine scans to be performed in a much shorter scanning time period, thereby increasing the throughput of hospital scanning facilities. In the newer field of positron emission tomography (PET), this invention permits the construction of more economical and more efficient scanning machines.

The improved detection efficiency of the scintillation camera is accomplished by making the camera plate thicker while at the same time maintaining good spatial resolution. The subject invention allows adapting the Anger camera principle to higher gamma-ray energies, including 511 keV. This allows construction of an economical scintillation camera which has both good spatial resolution and high efficiency. In addition, the novel camera design is flexible and is capable of performing both conventional single photon nuclear medicine studies and PET studies.

This invention relates to a scintillation camera which is useful for human organ imaging. The camera comprises: (a) a scintillator means of thickness coordinated to correspond generally with the energy of the gamma-rays received; (b) photodetector means for detecting the scintillation photons; (c) background light filter means positioned between the scintillator means and the plurality of photodetectors; (d) analog-to-digital converter network means which is capable of processing pulses from the plurality of photodetectors; and (e) means for analyzing each scintillation event before storing the information in a digital memory.

The camera can include reflecting means capable of transmitting gamma-rays and reflecting the resulting light photons at an angle about 180°. The reflecting means is optically coupled to the entrance face of the scintillation means. The reflecting means may be a corner reflector. The reflecting means may be milled or pressed into the gamma-ray receiving face of the scintillation means.

The scintillation means can be a crystal such as a thallium activated sodium iodide crystal, barium fluoride, cesium fluoride or bismuth germanate. The background light filter may be a fused fibre optic plate window also known as a fiberoptic foreplate. The fibres may be plastic of a diameter less than 3 mm. The fibres in the fibre plate may have a rectangular cross-section. The fibres of the fibre plate window may converge from the scintillator means toward the photodetector means.

The area of each photodetector may be between 0.25 and 1.0 cm. sq. The photodetectors may be arranged in columns and rows. The photodetectors may be of a continuous encoding type. The photodetectors may be the wires of a multi-wire anode photomultiplier. Summing amplifiers may be used to sum the signals in the columns and rows.

The invention is also directed to a method of analysing in detail the light spread distribution on the surface of a scintillator which has received and been activated by gamma-rays. The purpose of the analysis method is to estimate the three coordinates of the point of first interaction of each gamma-ray detected. The "point of first interaction" is taken to mean the point in the crystal at which the incoming gamma-ray first produces light. For events which interact by the photoelectric process, it is the only interaction point, but for some fraction of the events it is the first one of the two or more interaction points with light being emitted at each point. By using the details of the light distribution to approximately separate the first interaction point from possible subsequent interaction points, the subject invention attains substantially improved spatial resolution compared with conventional scintillation cameras which do not employ this method of separation.

DRAWINGS

In the drawings which illustrate certain specific embodiments of the invention:

FIG. 9 represents a computer listing produced by the data analysis program;

DETAILED DESCRIPTION OF SPECIFIC EMBODIMENTS OF THE INVENTION

The method is to record for each gamma-ray scintillation event an estimate of the position of the first interaction point in all three spatial dimensions. By including a determination of the depth-of-interaction in the scintillator, as well as the usual two transverse dimensions, a few large crystals can be used to replace the arrays of small crystals found in conventional ring tomographs. In addition to being less expensive, such large crystals should be superior in performance to the small crystal arrays they are replacing because the large crystals are equally sensitive to gamma-rays impinging at oblique angles to the surface. Efficient detection of such gamma-rays is needed to maintain full efficiency at the edges of the field-of-view of a large aperture ring tomograph.

Figure 1:
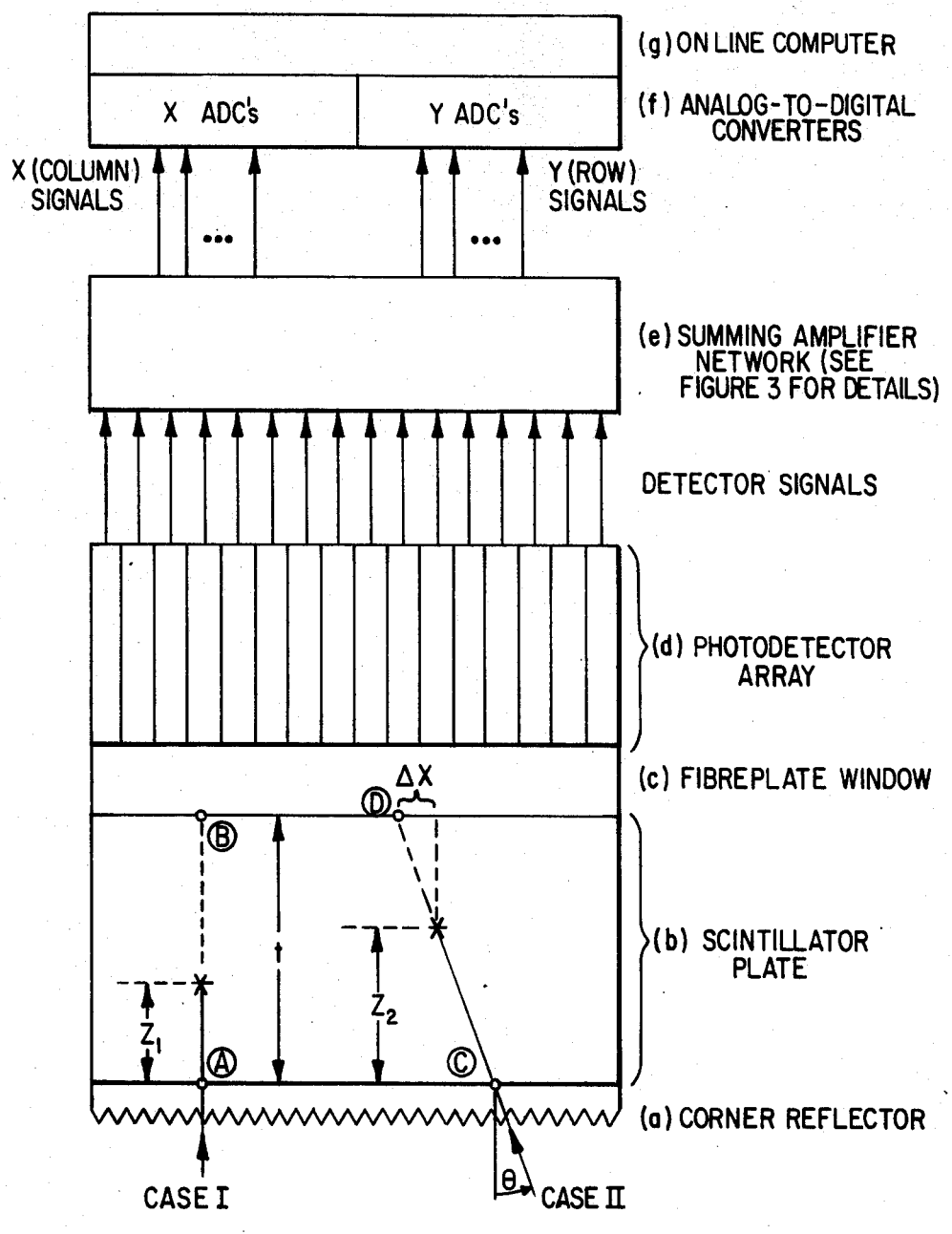
FIG. 1 represents a schematic view of the elements of the novel scintillation camera.

The novel scintillation camera design is shown schematically in FIG. 1. The principal components shown are (a) a corner reflector optically coupled to the crystal face where the gamma-rays enter; (b) a scintillator material (crystal) such as NaI, with thickness, t, appropriate to the energy of the gamma-rays of interest; (c) a fibre plate window (fiberoptic faceplate) optically coupling the crystal and the photodetector array; (d) an array of small photodetectors (on the order of 5-10 mm in size); (e) and (f), a linear summing amplifier and fast analog-to-digital converter (ADC) network to process the pulses from the photodetectors; and (g) a fast on-line computer to analyze each scintillation event before storing in digital memory.

Two types of gamma-ray trajectories are of interest. These are labelled as Case I and Case II in FIG. 1.

Case I is a normally incident gamma-ray, as would be selected by a parallel hole collimator (in a scintillation camera) or by the conjugate detector (in PET). To be detected, the Case I gamma-ray must interact with the scintillator material to produce as the scintillation event a light flash somewhere on the line segment AB. The exact depth of this first interaction along the line is different for each different detected gamma-ray. The invention is designed to measure for each detected event the depth-of-interaction, indicated for the Case I events by $Z_1$ in FIG. 1. This measured depth-of-interaction can be used to correct the calculated horizontal position for each event, i.e., to compensate for the loss of horizontal resolution due to different distribution of light characteristics at the photodetectors for gamma-rays interacting at different depths. Without such compensation, the ultimate horizontal resolution can only be obtained if the thickness (t) is chosen smaller than or on the same order as the desired resolution. Because of this characteristic, conventional scintillation cameras incorporate thin camera plates.

Case II events (shown in FIG. 1) are also important. By entering the scintillator along a non-normal trajectory, these events might be selected by a pin hole or slant hole collimator (in a standard scintillation camera) or by an off-center event in the conjugate detector (in PET). These events may first interact at any point along the line segment CD, as governed by the nuclear cross section and the laws of chance. In Case II, it is even more important than it was for Case I events to measure the depth-of-interaction ($Z_2$). With a knowledge of the angle of incidence ($\theta$) from the collimator or conjugate detector, the depth-of-interaction measurement can be used to correct for the horizontal error ($\Delta X$) caused by the projection of the light from the point of interaction onto the photodetector array. Without such correction, the resolution is worse for non-normal incidence ($\theta \neq 0$) than it is for normal incidence, which in turn forces the incorporation of still thinner and thus less efficient camera plates. By measuring the depth-of-interaction, the present invention allows a correction to be made to compensate for the horizontal error ($\Delta X$) inherent in detecting gamma-rays incident at non-normal angles, as in Case II.

For gamma-rays less than 1 MeV, and plates less than 10 cm thick, the scintillation light originates at a few (i.e. less than 5) point sources for each gamma-ray detection scintillation event. For NaI, the most probable number of points is one or two. The light falling on a plane surface of a plate of such a scintillator has an intensity distribution which is the sum of light from a small number of point sources. Given such a distribution in detail, the source distribution can be calculated by fitting a function of the unknown positions and intensities to the measured distribution. For single point distributions (i.e., photoelectric absorption of the incident gamma-ray) such a fit would yield three coordinates of a point on the initial gamma-ray trajectory, which is the information desired. For the case in which one or more Compton scatterings occur, the desired first interaction point quite likely corresponds to the point of light emission with the smallest Z-value (i.e., nearest the entrance window). This is because the most probable Compton scattering angle in the scintillator is around 20°, which tends to cause subsequent interactions to be deeper in the plate.

The detector of the invention is designed to provide the maximum useful amount of information about the light distribution on the surface of the plate coupled to the photodetector array, and to calculate from this measured data by means of an on-line realtime computer the three dimensional position of the point of initial gamma-ray interaction. For NaI, each photopeak event produces about 20,000 photons, half of which start toward the photodetector array. In the subject scintillator there are thus enough photons to carry a large amount of information about the original distribution of light sources.

Figure 2:
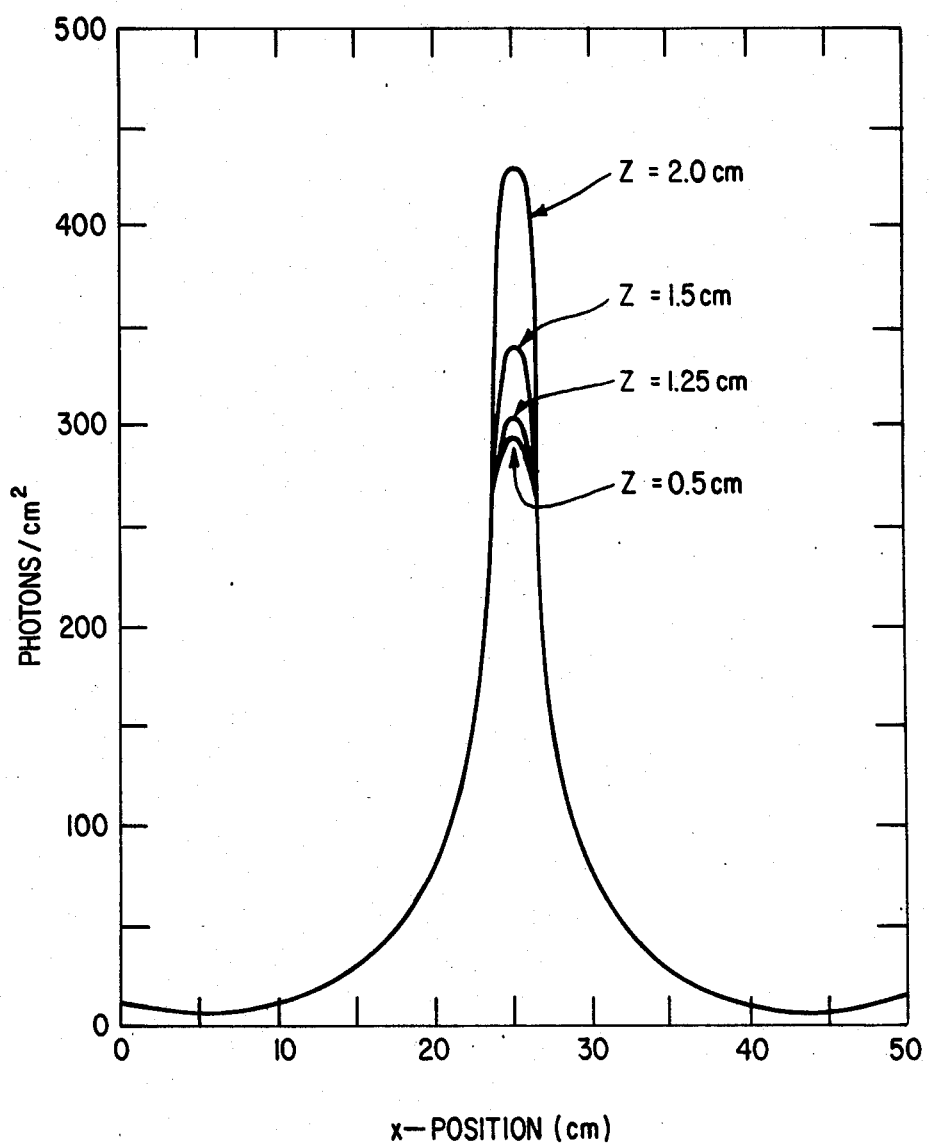
FIG. 2 illustrates in graphic form the calculated light distribution function on the rear face of a 2.5 cm. thick NaI scintillator for normally incident gamma-rays of 511 keV.

The physics of gamma-rays interacting and light propagating in materials is well known. The expected distribution of scintillation light sources and formation of light distribution on the photodetector array has been accurately calculated and reported in the literature (Yao Xiao Guang and Joel G. Rogers, "A Monte Carlo Calculation of Detector Design for PET", Nucl. Instrum. & Methods in Physics, 234, pp. 382-387 (1985), which is incorporated herein by reference. FIG. 2 (which is a reproduction of FIG. 3 in the aforementioned publication) shows the calculated light distribution function on the rear face of a 2.5 cm thick NaI scintillator for normally incident gamma-rays of 511 keV. The surfaces of this crystal are finished with the diffuse reflector, MgO, which is the standard surface finish for conventional scintillation camera plates. For single-step photoelectric absorption events, the calculation shows that events occuring at large Z (i.e.. near the photodetector array) produce a more sharply peaked light distribution than events occuring at smaller Z (i.e. nearer the entrance window). For conventional scintillation camera design, this depth variation is a contributing cause to the loss of resolution for the normal-incidence case when resorting to a thicker camera plate.

To avoid the variation of peak intensity with depth-of-interaction in the subject design, a corner reflector sheet is substituted for the MgO reflector on the entrance window. Corner reflector sheets are routinely used in plastic automotive and bicycle warning reflectors. Comprised of a pattern of cube corners pressed into transparent plastic sheets, these reflectors have the property that light reflected internally from any one of the cube sections returns along a ray direction parallel to the incident ray and is displaced at most by the dimension of one of the cube sections. The dimensions of the cube sections can be as small as is needed. For example, 2-3 mm which is typical for automotive warning reflectors is satisfactory. Used on the entrance window, a sheet of corner reflector creates an image of each point light source which coincides in position with the position of the light source and is slightly blurred by the 2-3 mm size of the cube corners. This removes the depth-of-interaction variation of the shape of the light spread function seen in FIG. 2. Because of the action of the corner reflector, each point source appears as a point source at the same position but twice as bright due to the addition of reflected light. The corner reflector preserves the depth information carried by the reflected photons. This improves the statistical accuracy of the depth determination substantially and makes possible the use of a simplified fitting procedure to separate the first interaction point from the possible subsequent interaction points.

An alternative implementation of the corner reflector concept would be to mill or press the cube pattern directly into the surface of the scintillator. This technique would prima facie be difficult to manufacture but has the advantage of avoiding some minor light loss due to reflections at the plastic scintillator interface. In addition, scintillators such as NaI have a higher index-of-refraction than plastic. Thus, a corner reflector of such material will reflect at a wider range of angles than plastic.

FIG. 2 also demonstrates another defect in conventional scintillation camera design. The light distribution contains long tails which form a position independent background far from the point of scintillation. These tails are caused by the emission of light which impinges on the glass window of the photodetector array near the critical angle of the NaI-glass boundary. This light is refracted to an angle nearly parallel to the surface and so travels in the glass window to a position far from the scintillator before being detected by the photodetectors. Detecting this light is obviously undesirable because it carries little or no position information and yet contributes to the electronic dead time of the detection system thereby reducing the counting rate capability. To eliminate this unwanted background light, the detector design incorporates a fibre plate window (also known as a fiberoptic faceplate) located between the scintillator and the photodetector array. Such plates are commercially available and are composed of standard glass fibres fused into a light absorbing extramural matrix. The plates have the property that they transmit light impinging at less than a selected numerical aperture angle and absorb any light impinging at a larger angle. The use of the corner reflector and the fibre plate optically decouple parts of a large camera plate in the longitudinal and transverse directions thereby enabling it to function more like a discrete detector array. This improves the count rate capability which becomes more important as the efficiency is increased. The fibre plate also improves the operation of the corner reflector by absorbing any light not reflected by the corner reflector because the light reaches the reflector at too great an angle.

The final elements of the detector hardware are the photodetector and signal processing electronics. The objective is to digitize the two-dimensional light distribution falling on the plate surface which is coupled to the photodetectors. From FIG. 2 it can be seen that the function which is to be digitized has large variations over distances on the order of 1 cm or less. The sampling interval must therefore be much finer than the 2-3 inch (50-75 mm) sampling interval found in conventional scintillation cameras. The optimal sampling interval depends on the quantum efficiency of the photodetectors and the amount of light received per area on the collecting surface of the plate, which in turn depends on the thickness and light conversion efficiency of the scintillator material employed.

To obtain a useful depth-of-interaction estimate, at least three samples must be taken for the narrowest of the light spread distributions, that is, the ones for interactions occuring deep in the plate (near the photodetector array). By obtaining at least three samples, both the centroid and the width of the light spread distribution can be independently determined. For single-interaction-point events, the width is proportional to the depth of interaction. For multiple-interaction-point events, the correspondence between width and depth is only approximate but a substantial resolution improvement is still possible by using the approximate depth information (derived from a width calculation) to correct the horizontal position determination. Light sources at a greater distance from the photodetector surface will be sampled by more than three detectors. For these events, a more complex calculation may be used to obtain a better estimate of the position of first interaction point.

A typical scintillation camera plate measures an area 1000 cm$^2$ or more. In the subject invention, samples are ideally taken at an area interval of 1 cm or less in two dimensions. This implies a cluster of 1000 detector elements or more, so it is necessary to provide a fast and economical means of digitizing and storing the resulting data. The invention ideally incorporates an array of small photodetectors of area 0.25 to 1.0 cm$^2$ each (depending on the factors discussed above). These detectors each sample a square or rectangular area and are optically coupled to the plate in aligned rows and columns (similar to the squares on a checkerboard) to cover one entire camera plate surface. Two signals from each photodetector are routed to a separate horizontal (x) and vertical (y) summing network, as indicated schematically in FIG. 3.

The summing network is composed of a summing amplifier for each row and each column of the rectangular photodetector array. It forms a set of x signals, each of which sums all the signals in a column, and a set of y signals, each of which sums all of the signals in a row. By this device, the number of required ADC's is reduced from $A/a$ to $2\sqrt{A/a}$ where "A" is the camera plate area and "a" is photodetector sampling area. For a practical example of $A = 1000$ cm$^2$ and $a = 1$ cm$^2$, the required number of ADC's is only 64 which is comparable in complexity to existing commercially produced scintillation cameras.

Figure 3:
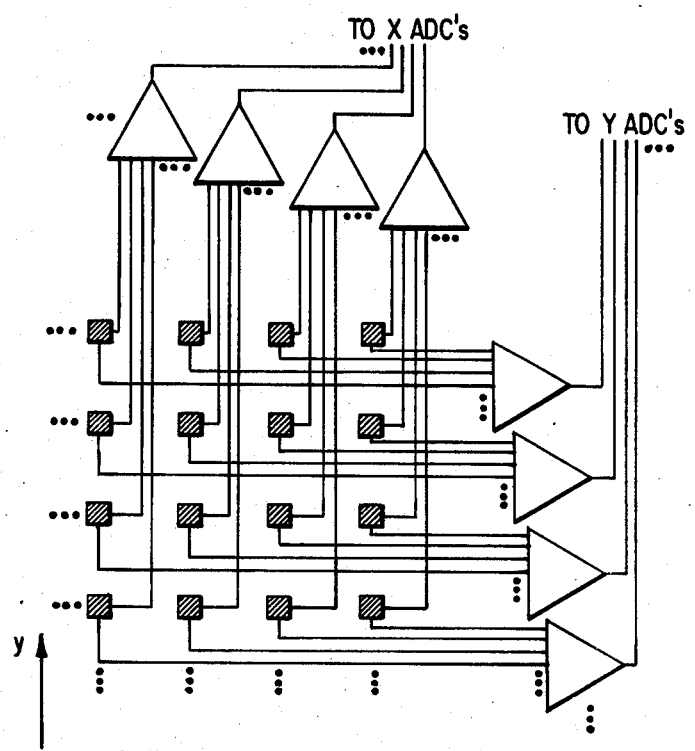
FIG. 3 illustrates in schematic manner the arrangement of photodetectors and horizontal (X) and vertical (Y) linear pulse summing amplifiers used to provide the summary network.

By summing the photodetector pulses as shown in FIG. 3, the invention approximately separates the two-dimensional sampling inversion problem into two one-dimensional problems. These simpler one-dimensional problems can be separately solved using an on-line computer for real time event-by-event analysis without compromising the rate capability of the detector.

A conventional computer algorithm can be used to calculate the x, y and z positions of the most probable first interaction point from the acquired data. The position of the intersection point is computed in software which can be developed further as required to suit the situation. Simple algorithms which can be used as a starting point demonstrate the principle of 3-D position encoding in the prototype to be discussed below. Optimum algorithms for computing horizontal position and depth-of-interaction can be developed as necessary.

The summing of the signals into separate rows and columns creates the effect of adjacent strip photodetectors of some selected width (on the order of 1 cm). Such strip detectors integrate all the light in one direction (i.e., along the strips) and sample the light at the intervals of the selected width. The relevant light spread function can be simply calculated for a point source under such conditions from the formula:

$$LSF(x) = \int_{-\infty}^{\infty} dy\, T(\theta) \cos^3\theta/(t - Z)^2$$

where $T(\theta)$ is the transmission function of the fibre plate for scintillation light leaving the scintillator at angle $\theta$. $T(\theta)$ is zero for incidence angles above the selected aperture angle ($\theta a$) of the plate and given by the Fresnel diffraction formula for angles less than the aperture angle. Z and t are as shown in FIG. 1.

Figure 4:
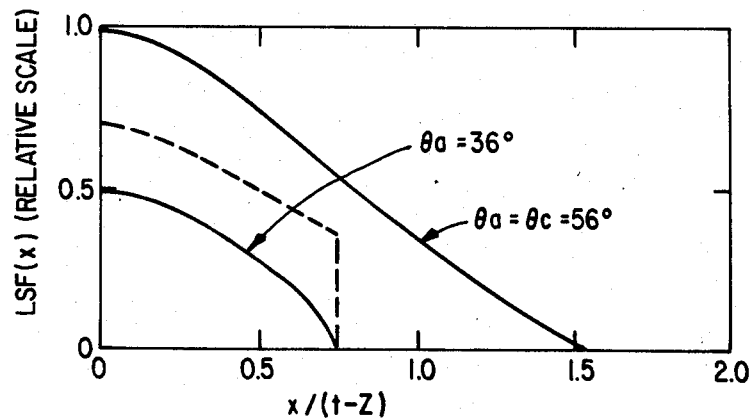
FIG. 4 illustrates in graphic manner relevant light spread function computed from an integral formula of fibre plate transmission function and selected aperture angle.

FIG. 4 shows the relevant light spread function computed from the above formula for the case of an available fibre plate with an aperture angle $\theta a = 36°$ coupled to a NaI scintillator. In addition to the $\theta a = 36°$ curve, a curve labelled $\theta a = \theta c = 56°$ shows the light spread function computed for a plain glass plate coupled to NaI. This latter case ($\theta a = \theta c$) is appropriate to a conventional NaI camera plate and therefore represents the present state of the art prior to the improvements of our invention.

FIG. 4 demonstrates the two main features of the invention. The width of the light spread function is inversely proportional to the depth of interaction (z) and the fibre plate ($\theta a = 36°$) eliminates the long tails found in conventional camera plates and creates a sharper edge to the light spread function. A still sharper cutoff, as shown by the dashed line, would be obtained with a fibre plate containing aligned square cross-section fibres instead of the round cross-section fibres that are currently available commercially. An aligned square cross-section fibre plate could be manufactured especially for this purpose and would result in an improved depth-of-interaction determination by making the width determination more precise.

FIG. 4 also shows that for single-interaction-point events the depth of interaction (Z) may be determined from the sampled light distribution in strip detectors in one dimension (x). The sampling of the light in the y-direction is redundant for the purpose of determining the depth of interaction for the simplest type of events (i.e., single-interaction-point photoelectric gamma-ray detection). The y-sampling electronics which is shown in FIGS. 1 and 3 is useful for analysing more complicated multiple-interaction-point events resulting from Compton scattering of the gamma-rays in the scintillator. However, for the purposes of economising on the number of photodetectors, it may be useful to provide strip detector sampling in only one dimension. The means to accomplish this is discussed more fully in a later section of this disclosure.

Prototype Design

To demonstrate the utility of the 3-D encoding principle, a prototype detector has been constructed and preliminary tests performed. The detector incorporates an array of 1×2 cm photomultiplier detectors (each one half of a Hamamatsu R1548 dual cathode photomultiplier tube). The scintillator plate incorporated in the prototype is an organic plastic scintillator available from the Bicron Corporation. An appropriate 5 cm thick NaI plate is available from the Harshaw/Filtrol Company. The principle of the detector can be demonstrated using readily available plastic scintillators and a detailed Monte Carlo calculation of the performance to be expected with the NaI crystal. In practice, plastic scintillators are inferior to NaI in their light conversion efficiency and thus it is expected that in a competitive commercial environment, an NaI crystal will be used in a practical detector for nuclear medicine.

Figure 5:
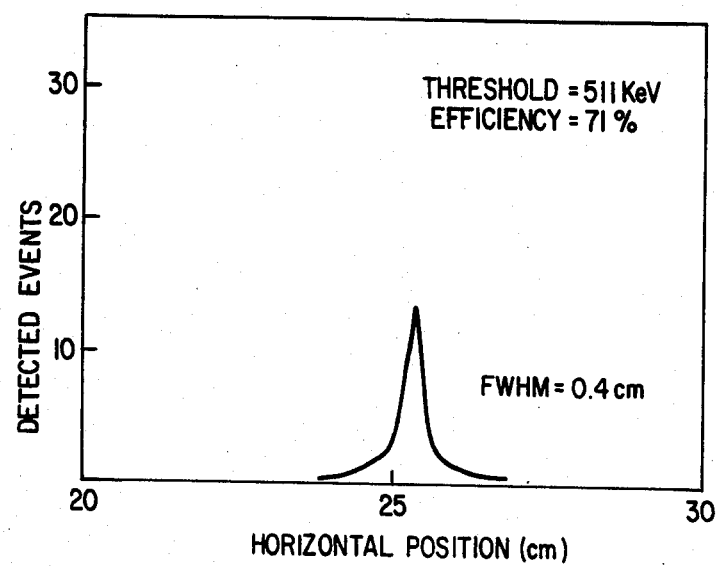
FIG. 5 illustrates in complementary graphic manner a Monte Carlo calculation of expected resolution of a 6 cm thick NaI camera plate.
Figure 5:
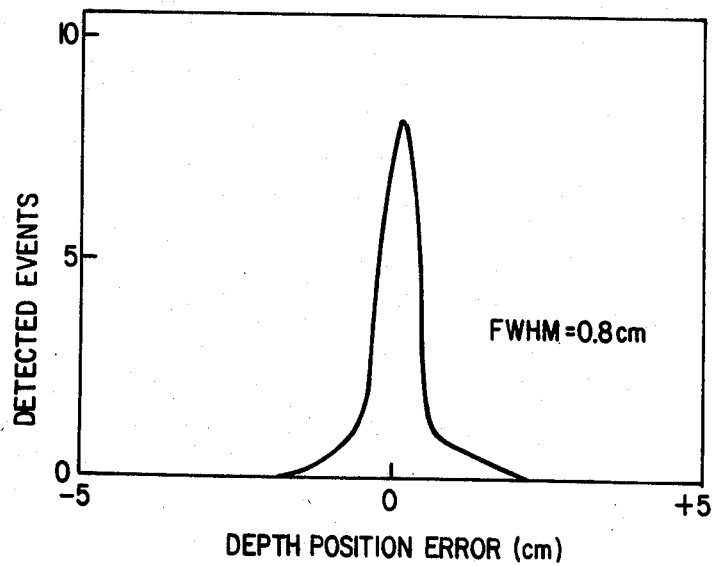

FIG. 5 shows a complete Monte Carlo calculation of the expected resolution of a 6 cm thick NaI camera plate, sampled at 1 cm intervals by small photomultiplier tubes. For a 511 keV collimated beam incident normally on the plate, the calculated horizontal resolution is 4 mm full-width-at-half-maximum (FWHM) and the depth-of-interaction resolution is 0.8 cm FWHM. The calculated efficiency is 71% which would correspond to 50% efficiency for coincidence detection in PET. The Monte Carlo procedure has been verified to be realistic by comparing calculated results with measured results for a 2.5 cm thick NaI bar detector. The details of this calculation and data comparison are stated in a publication by Yao Xiao Guang and Joel G. Rogers, entitled "A Monte Carlo Calculation of Design for PET", Nucl. Instrum. & Methods in Physics, 234, pp. 382–387 (1985), which is incorporated herein by reference.

Figure 6:
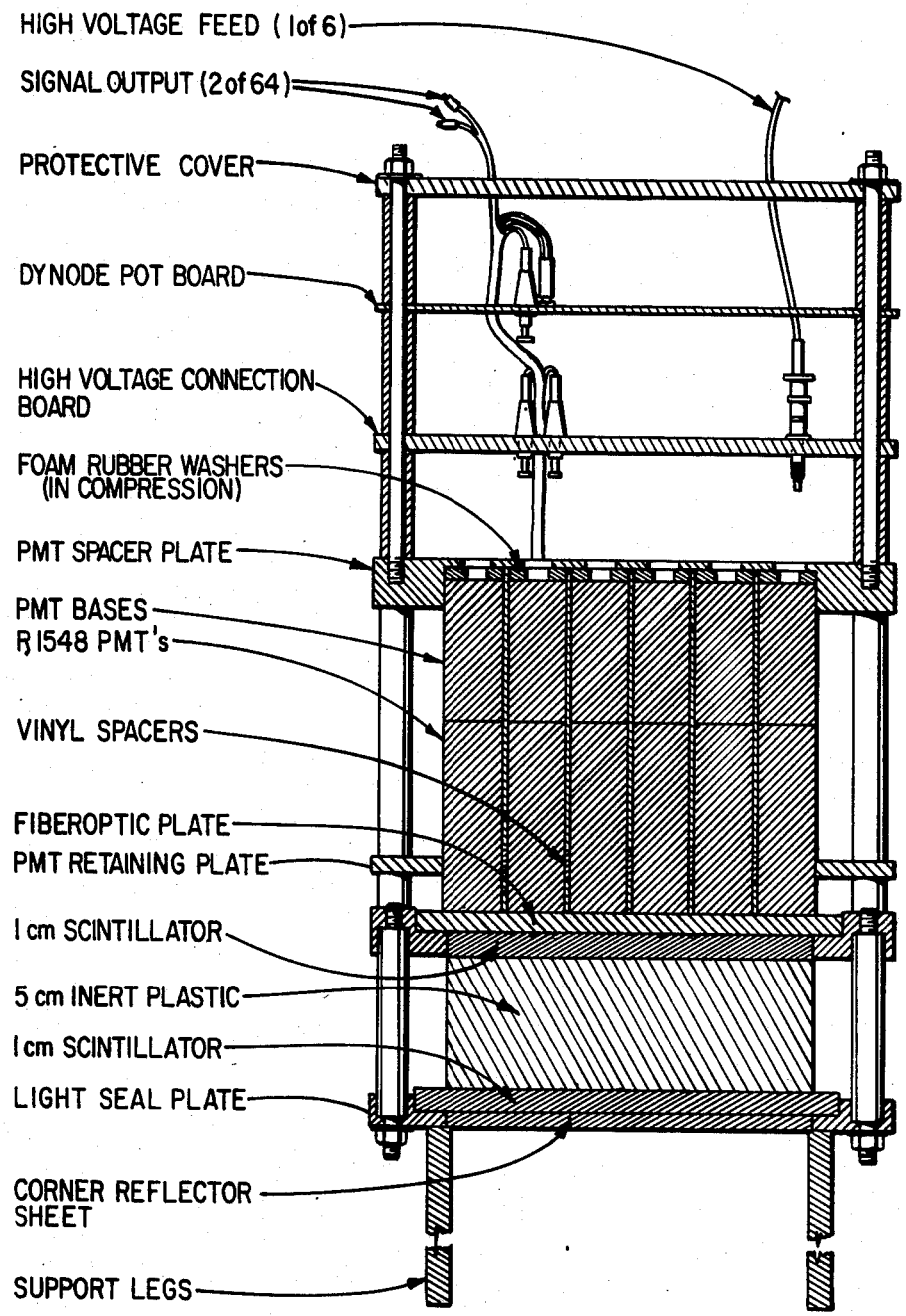
FIG. 6 represents a side section view of the assembly of the prototype detector.
Figure 7:
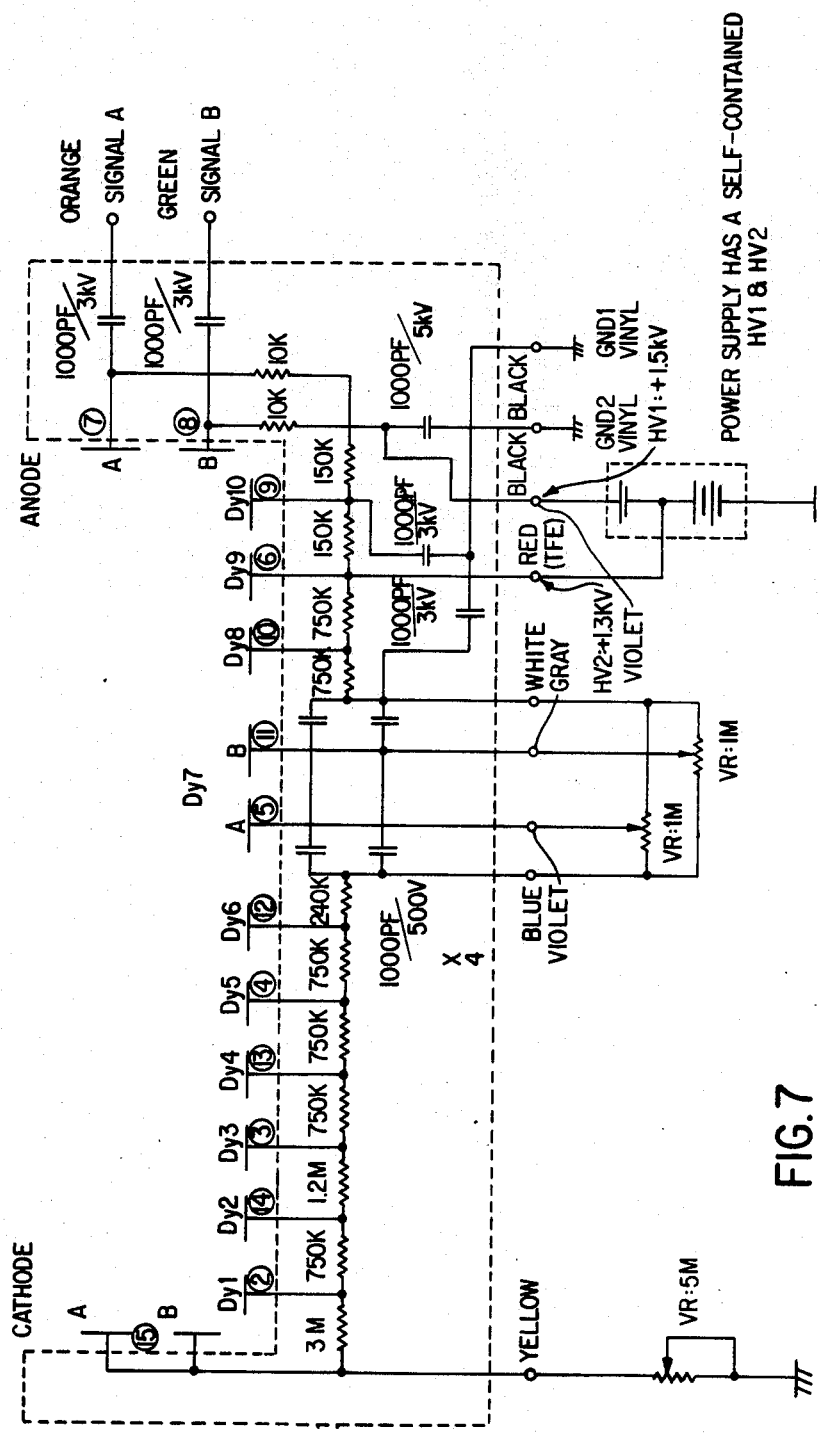
FIG. 7 represents the voltage divider networks for powering each PMT.

FIG. 6 shows an assembly drawing of a prototype detector as constructed by the inventors. The detector measures 16 inches high by 8.5 inches square with a scintillator area 7 inches square at the gammaray entrance window. The detector incorporates a layered plastic scintillator assembled with optical grease. Optical grease is also used to join the corner reflector to the scintillator at the entrance window, to couple the scintillator to the fibre plate, and to couple the fibre plate to the photodetector array. The photodetector array is a closely packed array of 1 inch square photomultiplier tubes (PMT's). These commercially available PMT's are arranged on a 6×6 matrix with the corners omitted, making a total of 32 PMT's in the entire assembly. Each PMT contains two independent photodetectors, each of area 1×2 cm. Each PMT is connected to a cylindrical tube base supplied by the same manufacturer (Hamamatsu). The tube bases contain the voltage divider networks for powering each PMT as shown in FIG. 7. Mechanical alignment of each PMT is provided by engaging the tube bases in a machined aluminum plate. Light seal and tension is provided by a foam rubber washer pressing on the end of each tube base.

Above the tube bases are two circuit boards (see FIG. 6) containing connectors and passive electronics for matching the signal gains of each of the 64 independent photodetectors. The tube bases are connected to the two circuit boards by 7 wires each, using miniature banana and miniature PC connectors. Signal gain matching is obtained by manually adjusting the three pots (shown in detail in FIG. 7) for each PMT, that is, a total of 96 pots.

To provide a light-proof enclosure and to reduce stray magnetic fields, the entire assembly is enclosed in a special alloy sheet metal (0.03" Conetic AA) box of dimensions 12×8.5 inches square. The box is joined with light proof seals at the top and bottom to the PMT Spacer and Light Seal plates of the assembly, which are also shown in FIG. 6.

The external voltage and signal connections are made by means of six foot long coaxial cables between the detector and a standard 19 inch instrument rack. The rack contains a regulated high voltage supply to provide power to the PMT's and signal processing electronics to receive the 64 independent photodetector signals.

The fibre plate is a 0.35" thick by 7.00" square glass plate manufactured by INCOM of Southbridge, Mass. The plate is specified to incorporate 8 micron glass fibres arranged perpendicular to the surface, to have a numerical aperture of 0.90, and a transmission factor of 70 percent for collimated white light.

The prototype is intended to demonstrate the principle of three-dimensional position encoding. For reasons of economy and to avoid long delivery times of certain essential components, the following three compromises were made:

(1) Selecting rectangular shaped, rather than square, photodetectors. In doing so, it is expected that the prototype will demonstrate good position resolution in only one transverse dimension (x) instead of two (x and y). Because the principle of the invention calls for summing the photodetector signals into symmetric and independent sets sampling narrow strips in x and y axes, it is only necessary to demonstrate the principle for either the x or y axes, not both. By choosing 1×2 cm photodetectors, good sampling (i.e., 1 cm wide strips) is provided only in one direction. This requires 50 percent fewer photodetectors to cover the detector area.

(2) To match the foregoing PMT characteristics, and to simplify fabrication, the corner reflector employed is also a one-dimensional version which focuses only in the x-axis.

(3) The detector utilizes a plastic scintillator instead of NaI. A 5 cm thick NaI plate was ordered from a normally reliable commercial supplier but delivery was delayed several months due to manufacturing errors at the supplier's factory. A plastic scintillator was used instead because it could be obtained commercially with shorter delivery. A BC-400 scintillator from Bicron was used with the following properties:

Scintillator: BC-400
Type: Plastic
Density: 1.032
Refractive Index: 1.581
Light Output, % NaI: 25
Decay Constant Main Component, ns: 2.4
Wavelength of Maximum Emission, nm: 423
H/C No. of H Atoms/No. of C Atoms: 1.104

In addition, plastic is not hygroscopic like NaI, so a special layered scintillator was easily assembled to demonstrate more clearly that depth-of-interaction determination is possible. The main problem with a plastic scintillator is that it produces only one-fourth as much light as NaI, so the measured resolution is expected to be worse than for NaI due to the poorer photon statistics.

Electronics Design

Figure 8:
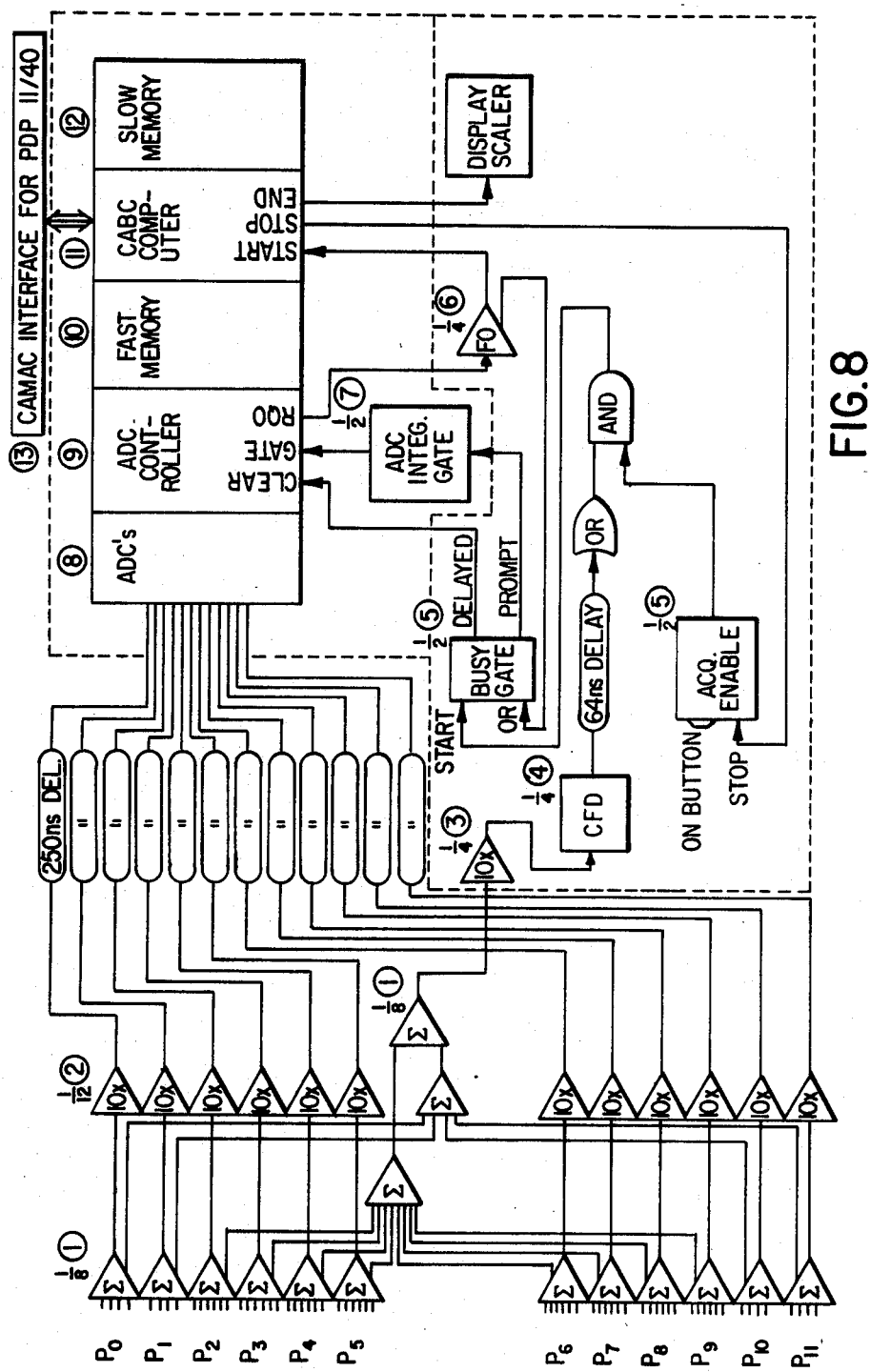
FIG. 8 represents a schematic diagram of the signal processing electronics of the camera.

The signals from the detector are carried to the electronics rack on 64 coaxial cables. The electronics processing of these signals is shown schematically in a block diagram in FIG. 8. The blocks (triangles, rectangles, etc.) in FIG. 8 represent commercially available NIM and CAMAC modules or portions of modules. For each block in FIG. 8, a circled item number identifies a corresponding entry in Table I below which gives the manufacturer's name and a brief summary of the module's functional description. In cases where a module contains several functionally identical units, a fraction precedes the item number in FIG. 8 to indicate that the block represents only a fractional portion of the module rather than the whole module. Connecting lines in the figure represent individual 50Ω coaxial cables carrying pulsed signals.

TABLE I
NIM and CAMAC Modules Referred to by Circled Numbers in FIG. 8 (Electronics Block Diagram)

NIM Modules

1. Lecroy Research Systems (LRS) Model 628 Weighted Analog Mixer consists of 8 independent sections. Each section is an 8-input, 2-output linear pulse summing amplifier with unity gain.

2. LRS Model 612A 12-Channel Photomultiplier Amplifier consists of 12 independent sections. Each section consists of a 1-input, 2-output pulse amplifier with a gain of 10.

3. LRS Model 335L Quad Amplifier consists of 4 independent sections. Each section is a 1-input, 1-output pulse amplifier with a gain of 10.

4. Ortec Model 934 Constant Fraction Discriminator consists of 4 independent sections. Each section is a 1-input, 3-output constant fraction discriminator. A front-panel screwdriver adjustment allows adjusting the pulse trigger level continuously from 30 mV upward. The discriminator setting is indicated by a voltage level presented on a front panel test point.

5. LRS Model 222 Dual Gate and Delay Generator consists of two independent sections. Each section is a multimode 3-input, 5-output gate generator. Used in one mode as the "busy gate", "prompt" output occurs at a small fixed delay following a "start" input. "Delayed" output occurs at a switch selectable delay following the start input. The "OR" input (if present at the end of the selected delay period) extends the selected delay period so that the "delayed" out occurs at the end of the "OR" signal instead of at the end of the selected delay period. Used in another mode as an ON/OFF flip-flop ("Acq. Enable"), the gate switching to the on state is caused by a front panel push button and switching to the off state is caused by a pulse input at the "stop" input of the Dual Gate and Delay Generator from the "CABC Computer".

6. LRS 429A Quad Mixed Logic Fan In/Fan Out generates multiple logic pulses, each identical to the corresponding input pulse.

CAMAC Modules

7. LRS Module 2323 Programmable Dual Gate and Delay generator consists of 2 independent sections. Each section is 4-input, 5-output multimode gate generator. One output occurs at a short delay following the start input with an output width which can be selected by the computer using CAMAC commands.

8. LRS Model 4300 16-channel Fast Encoding and Readout ADC (FERA) consists of 16 independent charge sensitive analog-to-digital converters (ADC) controlled by a common gate input. Each ADC integrates the charge during the gate period and converts the result to a 10-bit binary number in 4.8 microseconds. Data readout following conversion is accomplished using the model 4301 ADC controller (described below). Individual discriminator thresholds are set for each ADC via CA.MAC commands and sub-threshold outputs are suppressed from the readout.

9. LRS Model 4301 (FERA) ADC Controller provides an interface between the ADC (described above) and the "fast memory" described below. This module is connected to the other two by a high-speed ECL bus composed of a front panel flat cable. The module also provides level conversion between NIM levels (used in the gate generation electronics) and ECL levels (used in the ECL bus connections to the ADC's and memory). The module generates "RQO" output to indicate that the ADC's have converted valid (i.e., above threshold) data and are passing it to the fast memory.

10. LRS Model 4302 Triple Port Fast Memory unit. A front panel ECL bus provides 16-bit data storage into memory at a rate of 10 million words per second. The memory is connected to the "CABC Computer" (described below) by a second ECL port which allows the computer to read the data from memory at a rate of 5 million words per second. The "CABC Computer" also controls the busy state of the memory so that memory writing by the "ADC Controller" does not interfere with memory reading by the "CABC Computer".

11. LRS Model 4801 Fast Intelligent Crate Controller (CABC) is a programmable computer packaged as a CAMAC crate controller module. Occupying the control station of the CAMAC crate, the CABC can access all modules in the crate using standard CAMAC commands. The CABC is also interfaced to the PDP-11/40 host computer by a standard CAMAC branch highway cable connected to the front panel. The instruction execution speed of the CABC is 200 ns for addition, subtraction, and multiplication. It can also generate and sense the presence of NIM level pulses on 6 front panel connectors, three of which are used in this application for synchronizing the CABC software execution with the ADC gate generation electronics.

12. Creative Electronics Systems Model HM2161 Histogramming Memory is a 64K word by 24-bit memory. It is written by the "CABC Computer" using the CAMAC dataway and read by the PDP-11/40 computer using the CAMAC branch highway. Only the least significant 16-bits of each memory word are used in this application.

13. Kinetic Systems Model 2051 CAMAC Parallel Highway driver interfaces the UNIBUS of the PDP-11/40 computer to the branch highway connector of the "CABC Computer". This allows digital data to be read and written between the PDP-11 and modules in the CAMAC crate, including downloading programs into the "CABC Computer" itself.

The 64 lines entering the left of FIG. 8 represent the 64 coaxial cables from the detector. These are connected to 12 linear summing amplifiers, the realization of the amplifiers labelled "to X ADC's" in FIG. 3. For each detected scintillation event, each amplifier produces a current pulse which has a charge proportional to the light falling on a 1 cm wide strip at a particular x-position on the collecting surface. These 12 signals are amplified, delayed, and connected to 12 charge sensitive ADC's. For acceptable events, the 12 ADC's integrate and convert the 12 inputs in response to a common gate input.

The modules in the dashed box on the lower right of FIG. 8 comprise the ADC gate generation electronics. The input to this part of the electronics is the linear sum of all 12 strip signals, representing the total light collected for each event by the entire scintillator. If the total exceeds a selected threshold, this signal triggers a constant fraction discriminator ("CFD") which in turn triggers the "busy gate" (if it is not already busy and if acquisition has been enabled by the "ON button").

The integration time of the ADC is selected to be 60 ns, corresponding to the total rise and decay time of the plastic scintillator plus a comfortable margin for variation of signal delay through the different PMT's and amplifiers. The ADC's are gated on by any event satisfying the criteria of the gate generation electronics, namely, that the total light exceeds the discriminator threshold value and that the previous ADC conversions for any previous event have been read out of the ADC's by the "ADC controller". If the event does not meet these criteria it is ignored by the ADC's.

Once the ADC's have received a gate signal, they require a minimum of 7 to 9 microseconds for converting the inputs to 10 bits each and transferring the digital data to the "fast memory" (or longer if the "fast memory" is busy). The system is ready for the next event immediately after the data is transferred to the "fast memory". The ADC deadtime-per-event is 7 microseconds for an event of only one valid conversion and 9 microseconds for an event of 12 valid conversions. Any event can be processed by the ADC's in the range 7-9 microseconds. Faster ADC's are available from the same manufacturer.

Following the transfer of the ADC data to the "fast memory", an event exists as a list of binary numbers in the "fast memory". The structure of this list, determined by the specified functioning of the "ADC controller", is a word count followed by a word for each of the non-zero ADC conversions for that event. The word count tells how many of the 12 ADC's received a signal above their specified thresholds during the "ADC integration gate" time. A typical event consists of from 1 to 6 above-threshold ADC conversions. The "fast memory" enters a busy state following the completed transfer of an event list into it and will not respond to additional requests from the "ADC controller" until it is reset by the "CABC computer".

An important component of the electronics is the realtime computer shown as "CABC computer". This commercially available computer is packaged as a CAMAC module and may be programmed to perform any arithmetic operation on the list of ADC conversions stored by the "ADC controller" in the "fast memory". The minimum function that it must perform is to move the list out of the "fast memory" to free it so that the next event can re-use the space. Once it has cleared the event list from the "fast memory" it re-enables the "fast memory" to allow it to respond to the next event. The time it takes the "CABC computer" to completely process an event is the determining factor in the deadtime-per-event of the system. In acquiring the test data presented in the next section, the "CABC computer" was programmed to respond to an external signal from the ADC controller by taking the following steps: (1) fetch the data list from the "fast memory"; (2) obtain the number of valid ADC conversions for the event; (3) if the number is between specified limits, store a 12-byte list in the slow memory; (4) check if the slow memory is full and signal end of acquisition if so; (5) generate a front panel "End" pulse to signal that the event has been cleared from the "fast memory"; (6) re-enable the "fast memory" for the next event; (7) wait for the external signal again.

The ability to reject unwanted events in real time based on a complicated criterion is an important and powerful feature of the invention. For instance, such unwanted events might originate from gamma-rays which Compton scatter at an angle near 90° to produce a second scintillation at some distant point in the scintillator. (Compton scattering near 90° produces a symmetrical distribution of interaction points which cannot be resolved as to which occurred first.) If not rejected, such events would degrade the transverse position resolution because they produce a light at widely separated points.

The modules in the dashed box in the upper right corner of FIG. 8 are located in a standard CAMAC crate which is interfaced to a PDP-11/40 computer via a standard CAMAC branch highway and commercially available (Kinetic Systems) computer interface. A software program in the PDP computer controls the data acquisition by sending standard CAMAC commands to the modules in the CAMAC crate. The program in the PDP is in turn controlled by a human operator at a keyboard terminal. The main functions carried out by the PDP program in acquiring a single data set are as follows: (1) Download an event-by-event software program into the "CABC computer"; (2) Initialize the ADC's by writing a preset discriminator setting to each of them; (3) Enable acquisition by sending the total desired event count to the "CABC computer"; and (4) Transfer the acquired listmode event data from the CAMAC "slow memory" to a disk file at the end of the run.

Between the above steps (3) and (4) the event-by-event data acquisition among the ADC's, fast memory and slow memory is performed in the CAMAC crate by the downloaded program in the "CABC computer". The PDP computer does not participate in the event-by-event data acquisition. Event-by-event acquisition is initiated by the human operator using the "ON button" shown in FIG. 8. Data acquisition is terminated by the "CABC computer" issuing a signal when the stored program detects that the requested number of events have been acquired. Following the cessation of data acquisition at the end of the run, it is the human operator's responsibility to initiate at the terminal the sequence of tranferring the data set from the CAMAC "slow memory" to the disk for permanent storage. The "slow memory" capacity limits a single data set to a maximum of 10922 events. Each event in memory or on disk is comprised of 12 bytes, encoding each of the 12 strip detector signal amplitudes. The "CABC computer" supplies zero bytes to fill in positions in the event list corresponding to ADC's which received no signal above threshold.

Computer Processing of the Data

Each measurement (using a particular radioactive source configuration) results in a file of listmode data on disk. An off-line computer program was written which reads the data and processes it into histograms. In addition to calculating an estimate for the usual transverse (x) position of each scintillation event, the program also computes an estimate for the depth-of-interaction (Z) position of each event.

FIG. 9 illustrates a computer listing produced by the data analysis program. Operating in this mode, the program prints one line for each event. The first 50 events of a file of typical data were printed in this example. The columns headed "P0" to "P11" give the 12 ADC conversions for each event. A typical event is characterized by a cluster of 2 to 6 non-zero conversions with zeros on either side. The program calculates three parameters from each set of 12 conversions, as listed in the 3 columns on the right side of FIG. 9. The first parameter (PARAM1) is the sum of all 12 conversions, which is proportional to the total detected light for that event. The second parameter is the centroid of the 12 conversions computed as follows:

$$\text{PARAM2} = \left[ \sum_{I=0}^{11} i\, P_i \right] / (\text{PARAM1}) + 0.5,$$

which is an estimate of the transverse (x) position of the scintillation point for simple events composed of only one cluster of non-zero conversions. For more complicated events containing more than one cluster, the interpretation is ambiguous and so this parameter is not computed, as indicated by a "0.0" in the PARAM2 column of FIG. 9.

The final column in FIG. 9 (PARAM3) is the width of the cluster as determined by the total number of adjacent non-zero conversions. This parameter is proportional to the depth-of-interaction. (As for PARAM2, events with more than one cluster are not analyzed and have "0.0" in this column.) Events corresponding to a scintillation point near the photodetector surface (i.e., having penetrated deep into the scintillator) have a small value for PARAM3. Events corresponding to scintillation far from the photodetector surface (i.e., small depth penetration) have large values of PARAM3 as the light spreads out over a larger number of detector strips.

The processing of the test data (presented in the next sub-section) consists of computing the three parameters previously discussed for each of 10920 events in a data file. A histogram of counts versus parameter value is made in the computer for each of the three parameters and for all events satisfying selected criteria. The selected criteria may be varied, but typically consist of the requirement that the depth-of-interaction parameter (PARAM3) have a value between specified limits. Specifying small limits for PARAM3 selects only events occurring deep in the scintillator while specifying large limits selects only events occurring near the entrance window surface of the scintillator. Events not satisfying the selected criteria are skipped over and do not occur in the final histograms. After all 10920 events have been processed, graphs of the histograms of selected events are displayed on a video terminal and written to a file which can be later printed if hardcopy is desired.

Presentation of the Test Data

Figure 10:
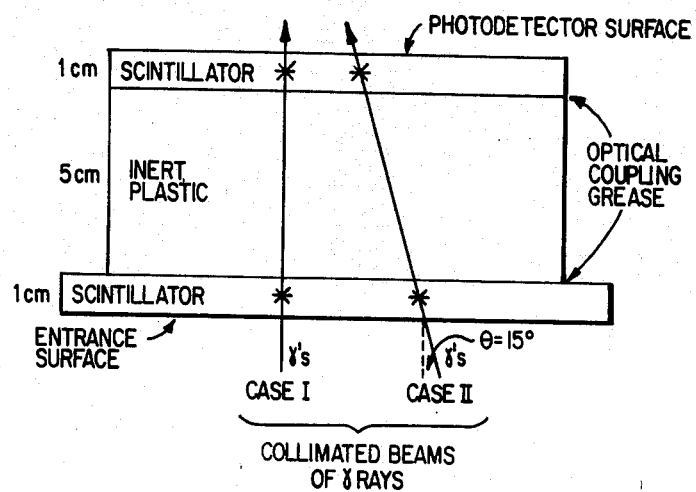
FIG. 10 represents in schematic manner plastic scintillator plates mounted on the prototype detector.

To demonstrate the principle of the invention, a special arrangement of plastic scintillator plates was mounted on the prototype detector as shown in FIG. 10. FIG. 10 shows three layers of plastic joined together by optical grease. The 7 cm thick plate consists of scintillating plastic in the first and last 1 cm layers with 5 cm of inert (i.e., non-scintillating) plastic between. This arrangement allows impinging gamma-rays to produce light near the "entrance surface" or near the "photodetector surface" but not in the intervening plastic. Once the scintillation light is produced, it propagates in the 7 cm thick medium just as it would in a single plate of 7 cm thick scintillator. By thus reducing the complete range of depth-of-interaction to only the two extreme limiting cases, the acquired data can be more easily interpreted to verify that the computed parameter (PARAM3) encodes the depth-of-interaction.

Figure 11:
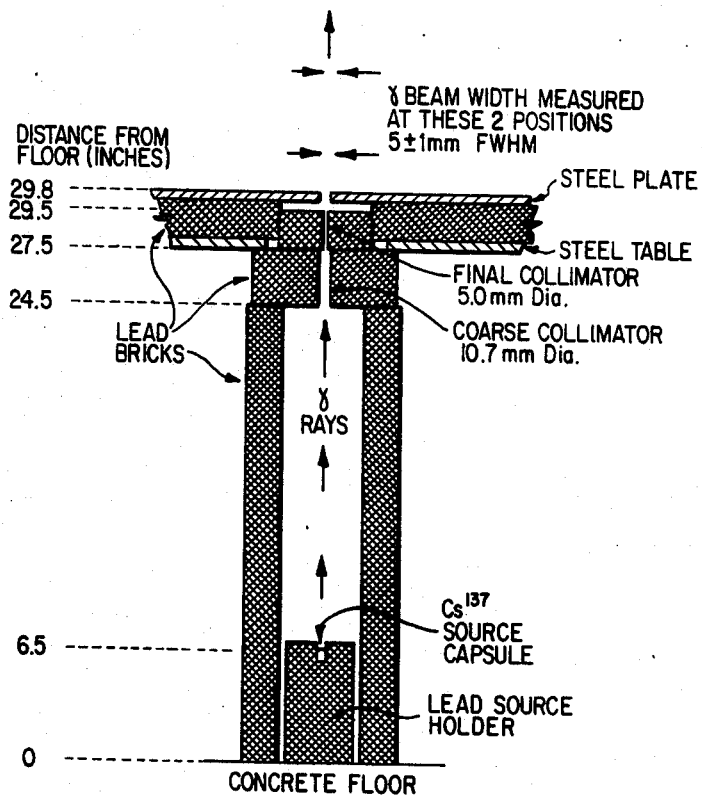
FIG. 11 illustrates in schematic manner the leadblock shielding arrangement used to form a collimated beam.

The detector performance was tested using a collimated source of 662 keV gamma-rays from a 19 mCi Cs-137 source capsule. FIG. 11 illustrates the lead block shielding arrangement used to form a collimated beam at the surface of the testing table. The source collimation was measured to be 5±1 mm full-width-at-half-maximum intensity throughout a 10 cm range of distances at the location above the table where the detector was tested. (This covers the entire range of distances occupied by any part of the 7 cm thick plastic plate containing the scintillators.)

The two types of measurements that are to be presented are shown in FIG. 10. In "Case I", the collimated source of gamma-rays is directed perpendicular to the entrance surface. In this case, the transverse coordinate (x) is the same for both possible depths of interaction. In "Case II", the collimated source is directed at a 15° angle off perpendicular, which causes the x-coordinate of the scintillation point to be different for the two different depths of interaction.

Figure 12:
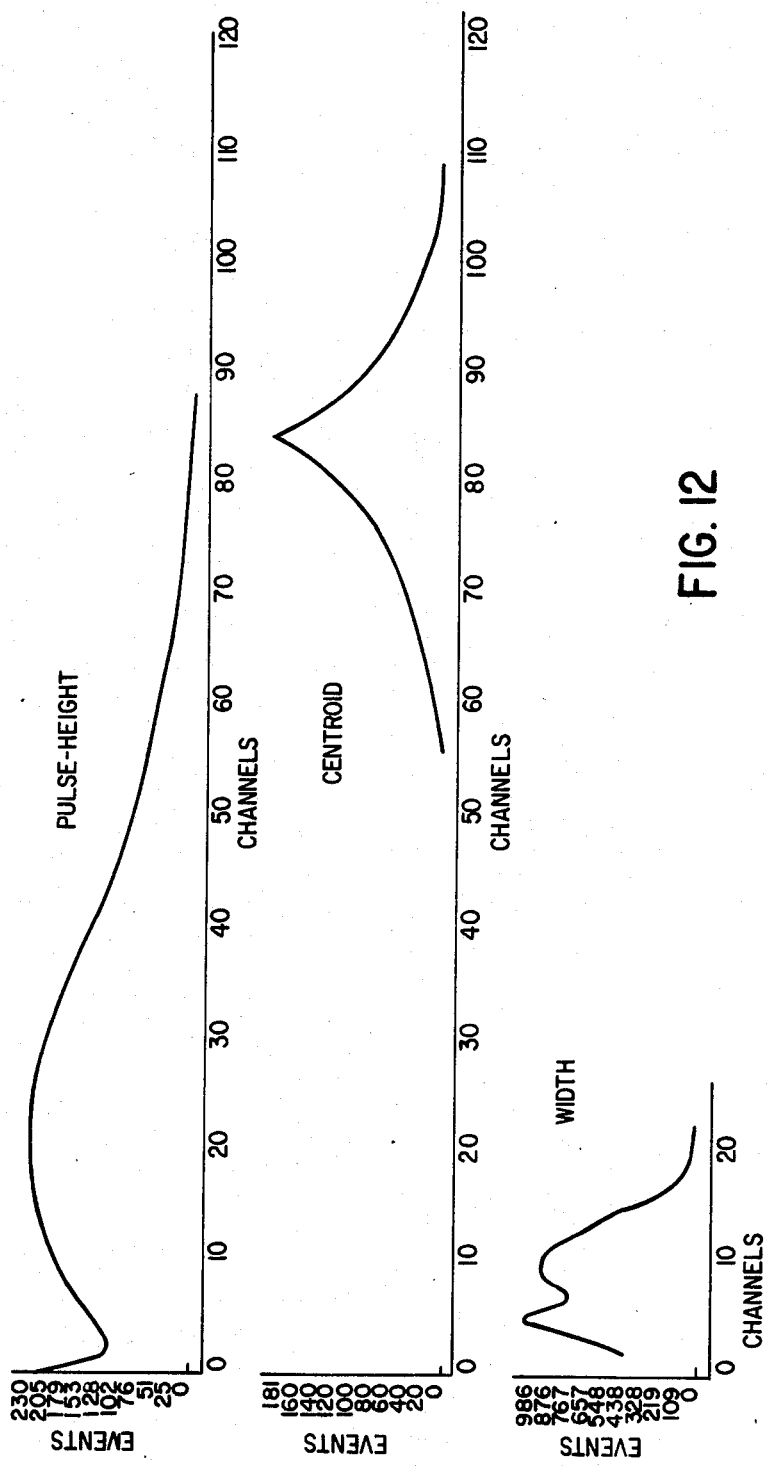
FIG. 12 represents a computer printout of a Case I analysis.

FIG. 12 shows a computer printout of the results of analyzing 10920 events acquired with Case I source configuration. The top graph is a display of counts versus the total of the ADC conversion, which was called PARAM1 in the earlier discussion of the analysis program. The middle graph is counts versus the CENTROID position, PARAM2. The bottom graph represents counts versus the ADC cluster WIDTH called PARAM3 in the earlier discussion. Here and in subsequent figures, the computer printouts have been modified only by adding hand drawn lines connecting the data points in an effort to smooth out somewhat the statistical variations of the data. It should be noted that the bottom WIDTH graph of FIG. 12 shows two peaks, corresponding to gamma-rays interacting at one or the other of the two possible depths required by the layered scintillator geometry.

Figure 13:
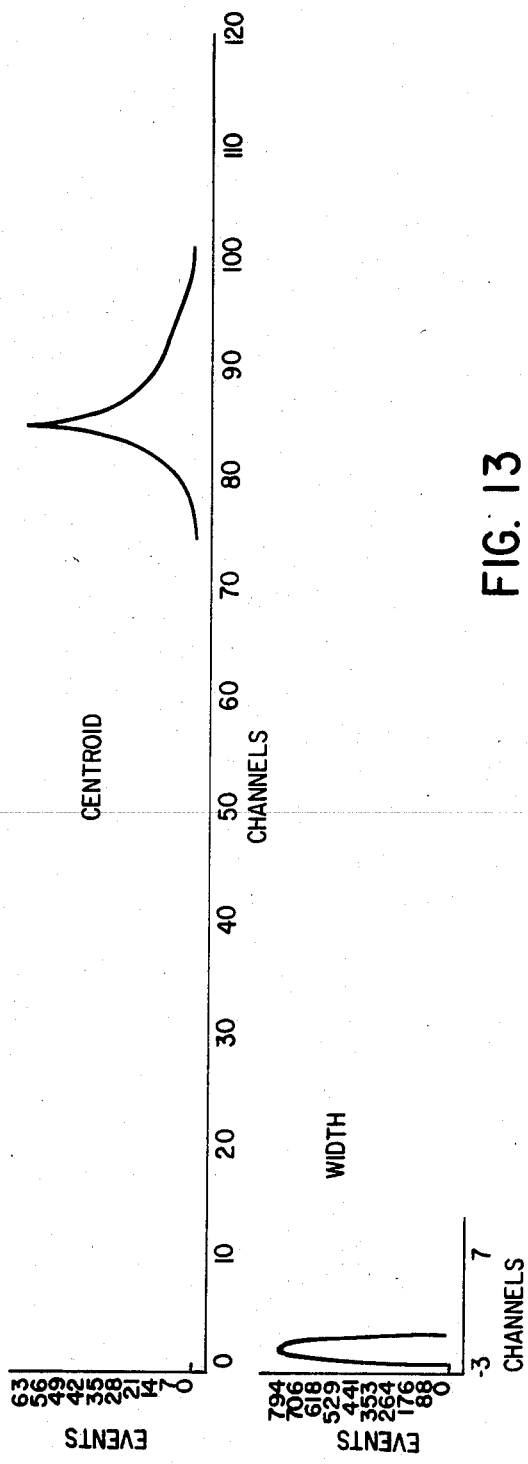
FIG. 13 represents a re-analysed computer printout.

FIG. 13 shows the same data file re-analyzed by requiring that all accepted events have a cluster WIDTH (PARAM3) of exactly 2. This selects events interacting in the second scintillator slab (the one near the photodetector surface.) There is only one peak in the bottom spectrum, as specified. In addition, the middle (CENTROID) spectrum is a much narrower peak (i.e., with better spatial resolution) located at the same position as the wide peak in the corresponding spectrum of FIG. 12. The reason that the transverse resolution is better for these selected events is believed to be due to the improved photon statistics for the events occurring closer to the photodetectors due to the fact that all the light is concentrated in only two detector strips as opposed to a larger number for the scintillations occurring in the first slab. With a more sophisticated algorithm for estimating the transverse position, it should be possible to improve the resolution for the remaining events, but no attempt has been made to optimize the algorithm beyond the simple centroid calculation discussed in the last section.

Figure 14:
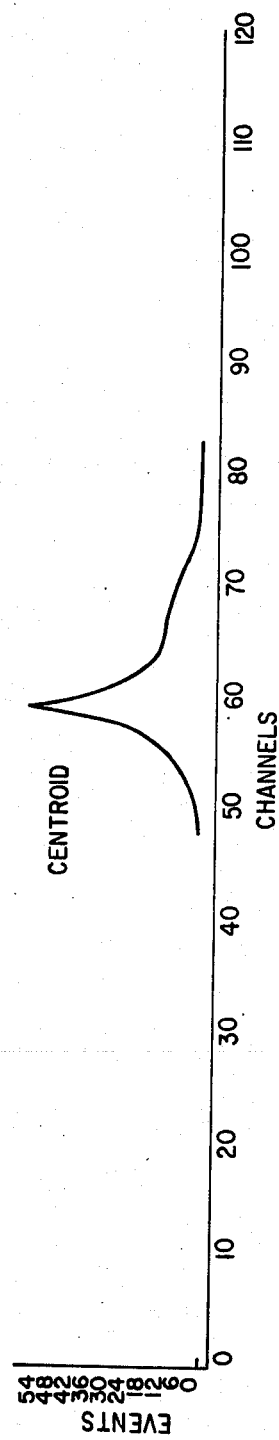
FIG. 14 represents a computer printout of a transversely shifted analysis.

FIG. 14 shows an identical analysis of a second data file acquired with the detector shifted transversely by 2.5 cm in X. It can be seen that the peak in the CENTROID spectrum has shifted by 26 channels compared to FIG. 13, which establishes the horizontal CENTROID scale as 1 mm/channel. The transverse resolution observed in FIGS. 13 and 14 is an impressive 5±1 mm full-width-at-half-maximum, even under these non-optimum conditions.

Figure 15:
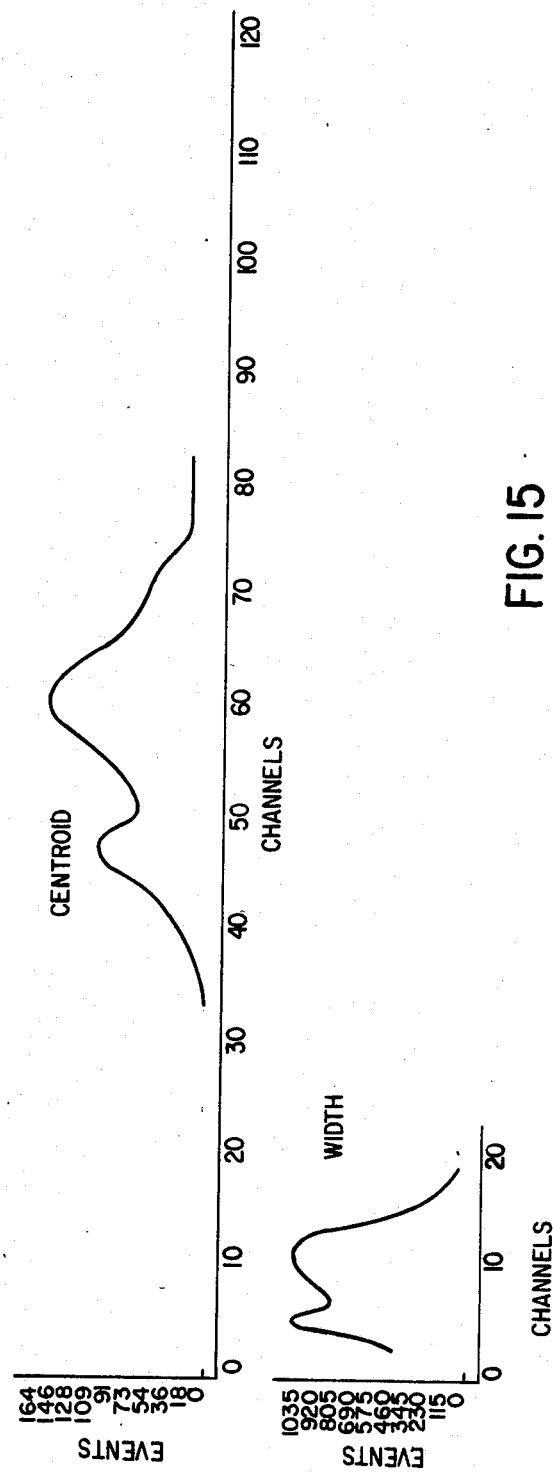
FIG. 15 represents a computer printout of data acquired by tilting the detector.
Figure 16:
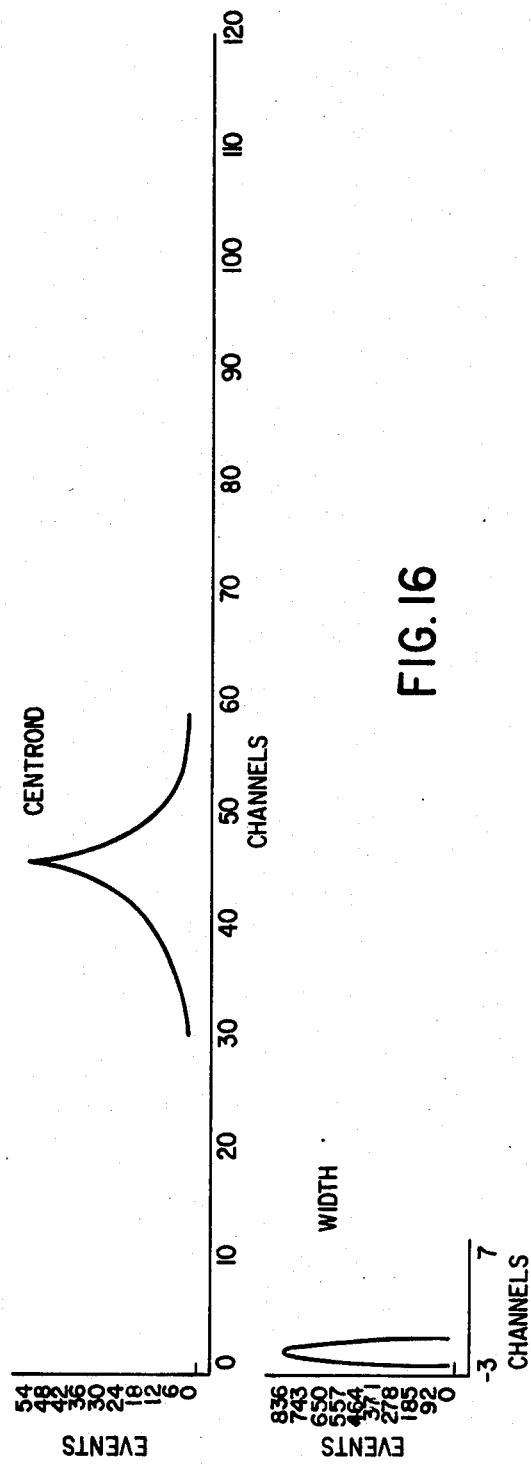
FIGS. 16 and 17 represent computer printouts of data obtained by separating the two peaks of the centroid graph of FIG. 15.
Figure 17:
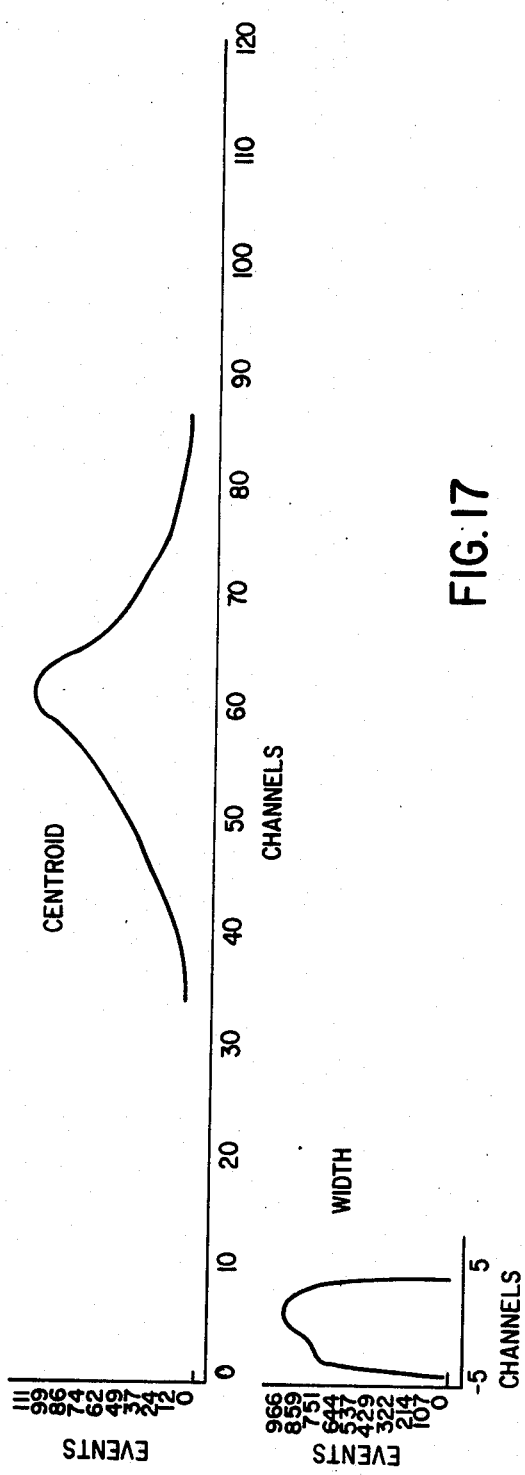

FIG. 15 shows data acquired with the detector tilted by 15° relative to the source collimation direction. Now both the CENTROID and cluster WIDTH graphs show two peaks because the tilt causes the two possible scintillation positions to become separated by a transverse distance, $\Delta X$, in addition to the depth separation produced by the intervening layer of inert plastic. To separate the two peaks in the CENTROID graph, events in the two peaks of the WIDTH graph are separately processed by the analysis program to form the two sets of graphs shown in FIGS. 16 and 17. The graphs of FIG. 16 contain events having small cluster width (selected by WIDTH =2), corresponding to scintillations occurring in the second scintillator (i.e., near the photodetector window). FIG. 17 contains events selected for large cluster width (WIDTH=3–6). The observed separation between the CENTROID peak positions in the two figures is 16 channels=1.6 cm. The expected separation can be calculated from the measured tilt angle of 15° and the known separation of scintillator plates (=6 cm from centre to centre). The expected separation is:

$$\Delta X = 6 \tan 15° = 1.6 \text{ cm}$$

which agrees well with the observed separation of the CENTROID peaks in FIGS. 16 and 17.

An analysis of the test data verifies that for the case of non-normal incidence (Case II) the measured depth-of-interaction information is sufficient to correct for the parallax error ($\Delta X$) caused by the variation in the position of gamma-ray interaction along the line of incidence. This demonstrates the practical usefulness of the inventors' new technique of encoding the depth-of-interaction in gamma-ray detectors for nuclear medicine.

Indicated Improvements That Might be Made to Prototype

Since the time the prototype was constructed (as discussed in the foregoing sections) new developments in photomultiplier tubes (position sensitive photodetectors) were announced in November, 1984 by the Hamamatsu T.V. Company, at the Nuclear Science Symposium of IEEE, published in the proceedings of that Symposium, H. Kume et al., "Newly Developed Photomultiplier Tubes with Position Sensitivity Capability", IEEE Trans. Nucl. Sci. NS 32, pg. 448 (1985), which is incorporated herein by reference.

The new PMT's incorporate multiwire anodes which integrate the light distribution falling on the cathode in 6 mm wide strips. In addition to the strip anode, the new PMT's can be made with a position sensitive last dynode, which determines the x and y centroid positions of the light distribution with an intrinsic resolution of 1 mm. A 15 cm square version of this PMT could be made to cover 25 percent of the photodetector surface of our prototype. Therefore, 4 such PMT's could replace the 32 we used in the prototype and provide even better position sampling (6 mm instead of 10 mm). The Hamamatsu Company can supply such PMT's at a very economical price.

Usage of the new PMT's will require a modification of the fibre plate used to couple the PMT's to the scintillator. Instead of parallel fibres perpendicular to the plate surface, a converging pattern of fibres will be required to concentrate the collected light slightly toward the centres of the 3" square PMT's. A separate converging fibre plate will be required for each PMT to homogenize the response of the detector in the regions between the PMT's. Converging fibre plates of construction similar to the parallel-glass-fibre plate used in the existing prototype are available commercially.

From both an economical and performance standpoint, it would be worthwhile to develop a special fibre plate for the invention instead of using the commercially available ones which are designed for much more demanding applications in photography and night vision. The fibre plate required could be assembled from extruded plastic fibres of square cross section and sizes on the order of 1-2 mm, by gluing the rods together with black epoxy of optical index chosen to give the desired numerical aperture angle.

An additional improvement to the prototype would be to couple the scintillator to the fibre plate using an air gap instead of optical grease. Because the fibre plate limits the angle of transmission to having values much smaller than the critical angle between air and scintillator, there would be very little light reflected at the interface even if the coupling medium is air. The reflections can be reduced even further by employng any standard lens coating material designed for that purpose. Using an air gap would allow the scintillator and corner reflector sub-assembly to be easily dismounted and exchanged for one of different thickness. Such an exchange capability is desirable in a single-photon scintillation camera detector to allow the scintillator's efficiency to be optimized for the wide range of different gamma-ray energies of interest in nuclear medicine.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A scintillation camera useful for human organ imaging comprising:
    (a) a scintillator means for receiving gamma-rays and generating photons of light for each gamma-ray scintillation event that occurs within the scintillator means, the means being of a thickness coordinated to correspond proportionally with the energy of gamma-rays received by the scintillator means;
    (b) an array of photodetector means for detecting the light spread distribution of the photons of light from the scintillator means and generating pulses in proportion to the light spread distribution of light detected, the spatial relationship between the array of photodetector means and the scintillator means being such that at least three of the photodetector means in any of the dimensions spanned by the array detect the light spread distribution from each scintillation event;
    (c) background light filter means positioned between the scintillator means and the photodetector means and optically coupled by an optical coupling medium to the scintillator means and the photodetector means;
    (d) means for analyzing the generated pulses representing the light spread distribution of each scintillation event to determine both the position of the centroid of the light spread distribution and the width of the light spread distribution; and
    (e) means for determining the depth of the point of first interaction for each received gamma-ray that produces photons of light within the scintillation means, the depth point being determined from thewidth of the light spread distribution for that first interaction.

2. A camera as defined in claim 1 wherein reflecting means for transmitting gamma-rays and reflecting the light at about 180° is optically coupled to the entrance face of the scintillator means.

3. A camera as defined in claim 2 wherein the reflecting means is a corner reflector.

4. A camera as defined in claim 1 wherein the scintillator means is a crystal.

5. A camera as defined in claim 1 or 2 wherein the scintillator means is a crystal selected from the group consisting of barium fluoride, cesium fluoride, bismith germanate, and thallium activated sodium iodide.

6. A camera as defined in claim 1, 2 or 3 wherein the scintillator means is a thallium activated sodium iodide crystal.

7. A camera as defined in claim 1 wherein the background light filter is a fiberoptic faceplate incorporating extramural absorption material.

8. A camera as defined in claim 2 wherein the reflecting means is pressed into the entrance face of the scintillator means.

9. A camera as defined in claim 1 or 2 wherein at least three photodetectors are used to sample the light from each scintillation event and the width of each photodetector is between 0.25 and 1.0 sq. cm.

10. A camera as defined in claim 1 or 2 wherein a plurality of photodetectors are used to sample the light from each scintillation event and the photodetectors are arranged in columns and rows.

11. A camera as defined in claim 1 or 2 wherein a plurality of photodetectors are used to sample the light from each scintillation event and the photodetectors are arranged in columns and rows and summing amplifiers are used to sum the signals in the columns and rows.

12. A camera as defined in claim 1 or 2 wherein the photodetectors are the wires of a multiwire-anode photomultiplier.

13. A camera as defined in claim 7 wherein the fibres in the fiberoptic faceplate window have a rectangular cross-section.

14. A camera as defined in claim 7 wherein the fibres of the fiberoptic faceplate are converging from the scintillator means toward the plurality of photodetector means.

15. A camera as defined in claim 7 wherein the fiberoptic faceplate is comprised of plastic fibres of a diameter less than 3 mm.

16. A camera as defined in claim 1 wherein the optical coupling medium between the scintillator means and the background light filter is air.

17. A camera as defined in claim 1 wherein the optical coupling medium between the background light filter and the photodetector means is air.

18. A method of analyzing the details of the light spread distribution on the surface of a scintillator which has received and been activated by gamma-rays for the purpose of estimating two or three spatial coordinates of the point of first interaction of each gamma-ray detected in the scintillator comprising collecting the light spread distribution utilizing a photodetector array optically coupled to a surface of the scintillator; analyzing the information collected by the photodetector array to determine both the position of the centroid of the light spread distribution and the width of the light spread distribution; and determining from the width of the light spread distribution the depth of the point of first interaction of each gamma-ray detection in the scintillator, the depth of the point being in relation to the surface of the scintillator through which the gamma-rays first entered the scintillator.

19. A method as described in claim 18 wherein the light spread distribution is sampled at intervals between 0.25 and 1.0 cm.

20. A method as described in claim 18 wherein the light spread distribution is sampled by photodetectors arranged in columns and rows.

21. A method as described in claim 20 wherein the columns and rows have a spacing of between 0.25 and 1.0 cm.

22. A scintillation camera useful for human organ imaging comprising:
  (a) a scintillator means for selected thickness for receiving gamma-rays of selected energy and generating photons of light for each gamma-ray scintillation event;
  (b) an array of photodetector means for detecting the light spread distribution of the photons of light from the scintillator means generated by the scintillation events and generating pulses in proportion to the light received, the spatial relationship between the array of photodetector means and the scintillator means being such that at least three of the photodetector means in any of the dimensions spanned by the array detect light from each scintillation event;
  (c) background light filter means positioned between the scintillator means and the photodetector means and optically coupled by an optical coupling medium to the scintillator means and the photodetector means;
  (d) analog-to-digital converter network means for processing the pulses from the array of photodetector means so that the light emitted by each scintillation event is sampled by analog-to-digital converters in any of the dimensions spanned by the array; and
  (e) means for analyzing the outputs of the analog-to-digital converter network for each scintillation event before storing the information about each event in a digital memory, said means including means for analyzing the generated pulses to approximate at least one of the transverse positions and the depth of the point of first interaction for each received gamma-ray that produces photons of light within the scintillator means.

* * * * *